United States Patent [19]
Jordan

[11] Patent Number: 5,423,334
[45] Date of Patent: Jun. 13, 1995

[54] IMPLANTABLE MEDICAL DEVICE CHARACTERIZATION SYSTEM

[75] Inventor: Guy J. Jordan, Alta, Utah

[73] Assignee: C. R. Bard, Inc., Murray Hill, N.J.

[21] Appl. No.: 12,541

[22] Filed: Feb. 1, 1993

[51] Int. Cl.⁶ ............................................. A61B 5/06
[52] U.S. Cl. ..................................... 128/899; 623/11
[58] Field of Search ...................... 128/668, 897–898, 128/899, 903, 748, 673, 653.4; 607/30–34, 60, 27; 623/11, 24

[56] References Cited

U.S. PATENT DOCUMENTS

| | | |
|---|---|---|
| 3,128,744 | 4/1964 | Jefferts et al. . |
| 3,299,424 | 1/1967 | Vindig . |
| 3,440,633 | 4/1969 | Vinding ................................ 340/258 |
| 3,689,885 | 9/1972 | Kaplan et al. . |
| 3,706,094 | 12/1972 | Cole et al. ...................... 343/6.5 SS |
| 3,752,960 | 8/1973 | Walton . |
| 3,805,301 | 4/1974 | Liebig . |
| 3,816,709 | 6/1974 | Walton . |
| 3,820,545 | 6/1974 | Jefferts ............................... 128/330 |
| 3,859,624 | 1/1975 | Kriofsky et al. . |
| 3,886,548 | 5/1975 | Majeau et al. . |
| 3,898,619 | 8/1975 | Carsten et al. . |
| 3,952,750 | 4/1976 | Mirowski et al. .................... 128/419 |
| 3,964,024 | 6/1976 | Hutton et al. . |
| 4,068,232 | 1/1978 | Meyers et al. . |
| 4,087,791 | 5/1978 | Lemberger . |
| 4,114,151 | 9/1978 | Denne et al. . |
| 4,129,855 | 12/1978 | Rodrian . |
| 4,187,854 | 2/1980 | Hepp et al. . |
| 4,196,418 | 4/1980 | Kip et al. ............................ 340/152 |
| 4,236,068 | 11/1980 | Walton ................................ 235/380 |
| 4,237,900 | 12/1980 | Schulman et al. .................... 128/673 |
| 4,242,663 | 12/1980 | Slobodin . |
| 4,262,632 | 4/1981 | Hanton et al. . |
| 4,281,664 | 8/1981 | Duggan . |
| 4,333,072 | 6/1982 | Beigel .............................. 340/825.54 |
| 4,361,153 | 11/1982 | Slocum et al. ....................... 128/419 |
| 4,373,527 | 2/1983 | Fischell ............................... 128/260 |
| 4,388,524 | 6/1983 | Walton . |
| 4,399,437 | 8/1983 | Falck et al. . |
| 4,425,117 | 1/1984 | Hugemann et al. ................... 604/93 |
| 4,473,825 | 9/1984 | Walton ............................ 340/825.54 |

(List continued on next page.)

OTHER PUBLICATIONS

B. C. Dillon et al., "Externally Powered Semiconductor Transponder", IBM Corporation Technical Disclosure Bulletin, vol. 20, No. 7, pp. 2525–2526, 1977.

*Primary Examiner*—Angela D. Sykes
*Attorney, Agent, or Firm*—Workman Nydegger & Seeley

[57] ABSTRACT

A system for enabling the acquisition from outside the body of a patient of data pertaining to a medical device implanted therein. A characterization tag is secured to the medical device prior to the implantation thereof. The characterization tag is powered by energy absorbed through the mutual inductive coupling of circuitry in the characterization tag with an alternating magnetic field generated outside the body of the patient. That circuitry in the characterization tag is selectively loaded and unloaded in a predetermined sequence of loading conditions that correspond to data about the implanted medical device. The alternating magnetic field is generated in a characterization probe, moveable external to the body of the patient. The probe includes electrical circuitry for sensing variations in the amount of energy absorbed from the field by the characterization tag. The characterization tag is secured to the exterior of the medical device by a biocompatible potting material in a characterization tag recess or, if the medical device is assembled from a plurality of constituent parts, by permanently capturing the characterization tag between a pair of these parts. Two single fluid reservoir access ports, a double fluid reservoir access port, a septum-less access port, and prosthetic hip joint are disclosed employing the system.

44 Claims, 13 Drawing Sheets

U.S. PATENT DOCUMENTS

| | | | |
|---|---|---|---|
| 4,494,545 | 1/1985 | Slocum et al. | 128/419 |
| 4,517,563 | 5/1985 | Diamant | 340/825.54 |
| 4,528,987 | 7/1985 | Slocum . | |
| 4,532,932 | 8/1985 | Batty, Jr. . | |
| 4,546,241 | 10/1985 | Walton . | |
| 4,561,443 | 12/1985 | Hogrefe et al. . | |
| 4,567,883 | 2/1986 | Langer et al. . | |
| 4,580,041 | 4/1986 | Walton | 235/480 |
| 4,618,861 | 10/1986 | Gettens et al. . | |
| 4,653,508 | 3/1987 | Cosman | 128/748 |
| 4,656,472 | 4/1987 | Walton . | |
| 4,679,560 | 7/1987 | Galbraith . | |
| 4,688,026 | 8/1987 | Scribner et al. | 340/572 |
| 4,692,147 | 9/1987 | Duggan | 604/93 |
| 4,695,955 | 9/1987 | Faisandier . | |
| 4,703,756 | 12/1987 | Gough et al. | 123/635 |
| 4,720,907 | 1/1988 | Rapp . | |
| 4,724,427 | 2/1988 | Carroll | 340/572 |
| 4,725,841 | 2/1988 | Nysen et al. . | |
| 4,730,188 | 3/1988 | Milheiser | 340/825 |
| 4,734,698 | 3/1988 | Nysen et al. . | |
| 4,746,830 | 5/1988 | Holland . | |
| 4,793,825 | 12/1988 | Benjamin et al. | 604/891.1 |
| 4,809,426 | 3/1989 | Takeuchi et al. | 29/568 |
| 4,854,328 | 8/1989 | Pollack . | |
| 4,857,893 | 8/1989 | Carroll . | |
| 4,863,470 | 9/1989 | Carter . | |
| 4,875,483 | 10/1989 | Vollmann et al. . | |
| 4,877,032 | 10/1989 | Heinze et al. | 128/419 |
| 4,918,416 | 4/1990 | Walton et al. | 235/497 |
| 4,941,201 | 7/1990 | Davis | 455/41 |
| 4,952,928 | 8/1990 | Carroll et al. . | |
| 4,992,794 | 2/1991 | Brouwers . | |
| 5,016,634 | 5/1991 | Vock et al. | 128/419 |
| 5,019,813 | 5/1991 | Kip et al. . | |
| 5,024,224 | 6/1991 | Engebretson . | |
| 5,028,918 | 7/1991 | Giles et al. . | |
| 5,041,826 | 8/1991 | Milheiser . | |
| 5,055,659 | 10/1991 | Hendrick et al. . | |
| 5,080,096 | 1/1992 | Hooper et al. . | |
| 5,084,699 | 1/1992 | DeMichele . | |
| 5,095,309 | 3/1992 | Troyk et al. . | |
| 5,103,222 | 4/1992 | Hogen Esch et al. . | |
| 5,105,190 | 4/1992 | Kip et al. . | |
| 5,105,763 | 4/1992 | Poiesz et al. . | |
| 5,124,659 | 6/1992 | Frola et al. . | |
| 5,153,583 | 10/1992 | Murdoch . | |
| 5,300,120 | 4/1994 | Knapp et al. . | |

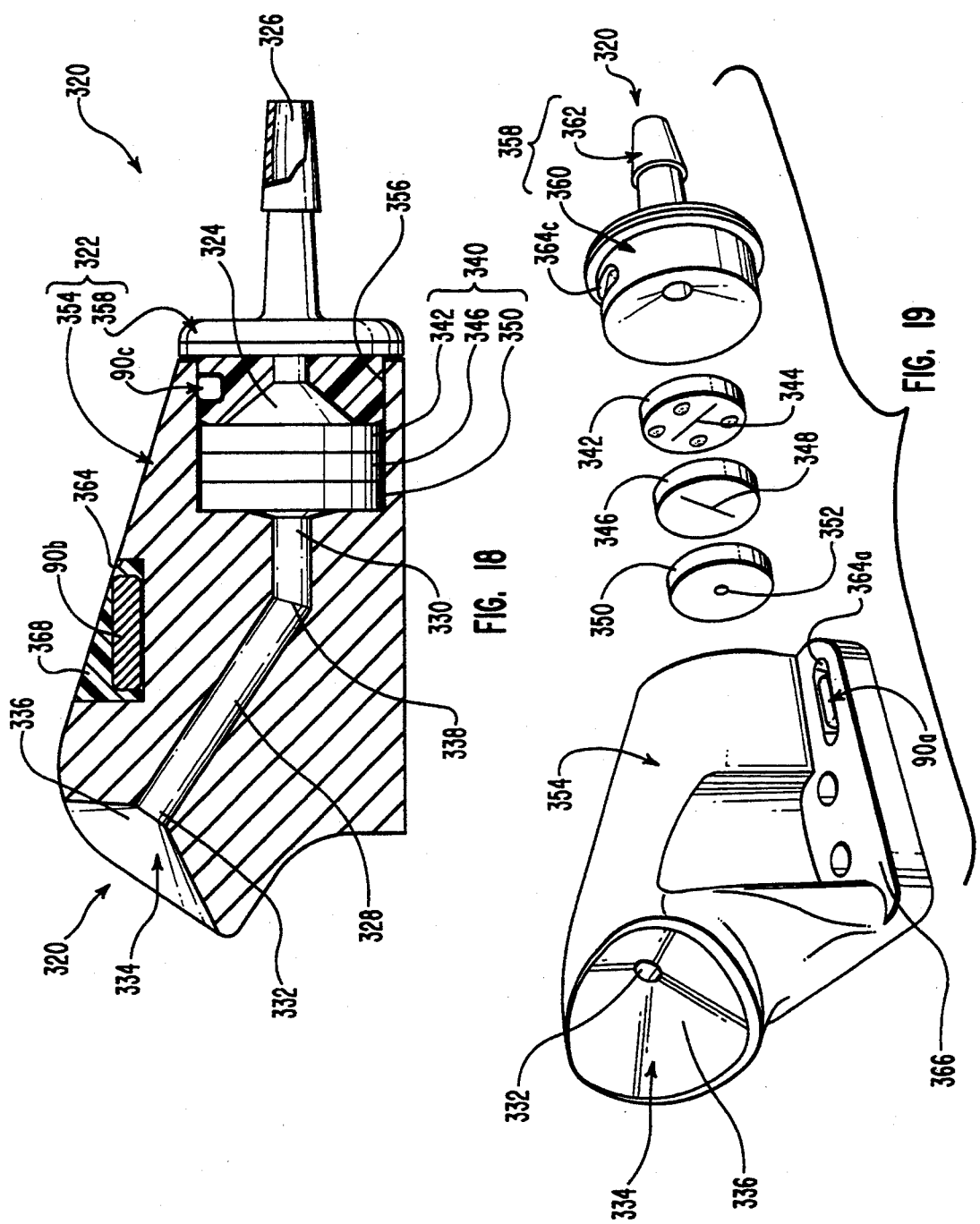

IMPLANTABLE MEDICAL DEVICE CHARACTERIZATION SYSTEM

BACKGROUND

1. The Field of the Invention

This invention relates to systems, devices, and methods for enabling the acquisition from outside the body of a patient of data pertaining to medical devices implanted therein. More particularly, the present invention relates to a system in which an implanted medical device, such as an infusion port or a prosthetic implant, may be identified or otherwise characterized by data obtained from outside the body of a patient using a hand-held medical device characterization probe.

2. Background Art

The medical use of implantable devices in human patients is steadily increasing. In addition, due to technological advances in implantable medical devices, the implanted duration of the residency of such devices is also lengthening.

Examples of such implantable medical devices include artificial heart valves, prosthetic joints, vascular grafts, artificial ligaments and tendons, urinary and gastrointestinal tract sphincters, vena cava blood filters, penal implants and other tissue expanders, fistula and hernia repair devices, implantable infusion ports with associated long term catheters, defibrillator catheters, demand pacer heart leads, as well as nonpassive implantable devices, such as artificial hearts, pacemakers, and medicament pumps.

As the use of this wide variety of implanted devices becomes more common and frequent, certain associated problems can be anticipated. That to which the present invention is directed relates to ascertaining the identity of such devices after the implantation thereof, or to obtaining other characterizing data about the implanted devices. Reasons for needing such an identification or such data will be discussed below, along with some of the constraints imposed by medical practices on the process of doing so.

The very reason for the installation of an implantable medical devices is to provide for a repeated function that is required by the body of the patient on the long term basis. Thus, medical devices are implanted, so that the accomplishment of such functions does not require excessively frequent therapy procedures. In some cases, such as with a prosthetic implant or a demand pacer heart lead, the medical device installed provides a function required on a continuous basis.

The implantation of any such devices, however, causes significant trauma to the patient. Thus, once implanted, there is a accordingly an incentive to avoid reaccessing such devices through any surgical reopening of the body of the patient.

Some implanted medical devices, such as implantable access ports and the long term catheters associated therewith, are nevertheless accessed to a very limited degree on a regular and repeated basis using specialized access tools that penetrate the skin of the patient to the access port. These are specifically adapted for correct interaction with each respective type of access port. Such access tools include needles and semi-rigid catheters, each in varying sizes adapted to a specific access port. The access tools penetrate the skin of the patient at the implantation site and then are used, respectively, to infuse fluids into or to withdraw fluids from the access port.

Palpation may be used to locate some implanted devices, and patient memory and the medical records, if available, can provide further information relative thereto. Nevertheless, to date, a marked lack is apparent in the field of implantable medical device technology of systems, devices, and methods that successfully enable the acquisition of data from outside the body of the patient, where that data pertains to medical devices implanted therein.

For example, different implantable devices are recommended for installation at the same implant location in the body of a patient. Thus, regardless of the use to which a device may be applied, the discovery of the implant location of that device, which is typically achieved by palpation of the body of the patient, is inadequate to identify that device or otherwise to supply characterizing data relative thereto. Such information is, however, essential to medical personnel providing post-implantation therapy that involves the device. Only with accurate and complete information about an implanted device can medical personnel adopt appropriate procedures, administer correct medicaments, and use proper, complementary access tools. A case in point will serve to illustrate.

The access ports associated with several types of infusion systems are frequently placed in the chest of the patient. Nevertheless, the catheter associated with such an access port may extend through the cardiovascular system to the vena cava, to the body cavity for peritoneal therapy, or alternatively to numerous other possible sites. As palpation can locate only the access port, and not the catheter associated therewith, the identity or purpose of an access port implanted in the chest of a patient is not immediately apparent, even when the implant site has been located.

If radiographic equipment is available at the site of any therapy associated with the access port, radiographic viewing of the patient can sometimes be of assistance. Radiographic view systems are disadvantageously large, rendering impossible the use of such systems to derive information about an implanted medical device, when the patient in whose body that device is implanted is not at or cannot be readily brought to a site at which radiographic viewing equipment is available.

Also, radiographic viewing of the implantable access port itself is usually incapable of providing any detailed information about the access port or the catheter attached thereto. If the profile of the port is not distinctive, then only if the implanted catheter is radio-opaque, can radiographic viewing assist medical personnel in identifying or otherwise deriving characterizing data relative to the infusion system.

Two risks are associated with post-implantation therapy utilizing an implanted access port, where the full nature of the implanted system is unknown. First, such access ports require use of a correct corresponding access tool: a needle or a semi-rigid catheter, each of various sizes or constructions. The use of an improper type of access tool with an access port, can result in damage to the access port or to the catheter attached thereto. At the very least, the use of an improper access tool rapidly accelerates the aging of the implanted access port.

Even if an appropriate type of access tool is utilized to penetrate the tissue of the patient and interact with the access port, the location of the distal tip of the catheter associated therewith will determine the proper type of any infusate to be injected into the port. Catheters extending through the cardiovascular system to the venae cavae are most frequently utilized for chemotherapy, so that a chemotherapeutic medicament should be injected into the access port associated therewith. On the other hand, if the catheter associated with such an implantable infusion port extends into the epidural space, for the purpose of providing periodic anesthesia there, the accidental injection of chemotherapeutic medicaments would certainly have disastrous consequences. Implantable ports with attached catheters extending into the body cavity for peritoneal therapy may need to be injected with antibiotics or other solutions, but never anesthesia or chemotherapeutic medicaments of the vesicant variety.

Clearly, the discovery of an implanted medical device in the body of a patient does not adequately identify or otherwise characterize that port, so as to enable medical personnel to practice post-implantation therapy without disastrous risks to the patient.

It might be presumed that the knowledge of a patient of the nature of the implant medical devices in the body thereof could be used to guide medical personnel. Nevertheless, this is not actually the case.

While a patient may know a substantial amount of information about a medical device implanted in the body thereof, frequently that information is not of the detail required to enable medical personnel to conduct post-implantation therapy procedures with correct access tools and correct dosages of medicaments.

The medical environment in which implants are prescribed and installed are unfamiliar surroundings in which many patients are ill at ease. Often the circumstances requiring the implants accompany severe disease or the discovery of such in the body of the patient. Under these stressful circumstances a clear and accurate understanding of the nature of an implant is often lost on the very recipient thereof.

Even if a patient is fully aware of the location, identity, and technical specification of a medical device implanted in the body thereof, that patient may be unable to communicate such information to medical personnel at a post-implantation therapy institution due to language or cultural barriers.

It is not uncommon that patients with implanted medical devices do not even retain a clear memory of the purpose of the implanted device. In extreme cases, a patient may be mentally incapable, either due to age, drug use, or other psycho-physical condition. Patients involved in accidents or severely ill patients may lack any consciousness whatsoever. Nevertheless, under all such conditions, the existence of an implanted medical device in the body of a patient suggests a need for possibly immediate, but certainly regular, therapy activities.

The increasingly long duration of some medical implants raises other concerns.

First, a patient, particularly an elderly patient, is likely to carry in the body thereof a plurality of implanted medical devices located at a corresponding plurality of implant sites. When such a patient is treated by any medical personnel, it is important initially an to ascertain the identity of or secure other characterizing data about each and every such implanted medical device.

Not only as discussed above is it necessary to have a relatively high level of certainty as to the appropriate procedures, medications, and access tools to be used with each, but it is possible that the timing of post-implantation therapy procedures for one such implanted device must be adjusted for the timing of such procedures associated with another implanted medical device. Otherwise, disastrous consequences, such as, adverse drug interactions are possible. Where such a patient is either mentally impaired, unconscious, or even just not completely informed as to the specification of each implanted medical device, the task of inventorying these devices and selecting appropriate sets of procedures at compatible times is increasingly demanding.

As a patent carrying an implanted device moves from one location to another, a device implanted at one institute will later be involved in post-implantation therapy at another institution.

Reliance on the memory of the patient to identify implanted devices is not always wise or feasible. Other sources of information about the implanted devices must be accessed before post-implantation therapy can safely ensue. It would appear that such a source of information might be locatable in the medical files of the patient.

Nevertheless, medical files for any given patient may not be current, or may not have travelled with the patient from one medical therapy institution to another.

While adequate information about implanted medical devices may in due course become available to medical personnel, many post-implantation therapeutic activities cannot be postponed until the convenient time that medical records have been located and then transferred between medical institutions. Those institutions may be situated in remote cities or countries, and obtaining the cooperation of such remote institutions may be quite difficult. Often business hours in distant time zones may not even overlap. In the meantime, a patient with an implanted medical device may be forgoing urgent post-implantation therapy procedures.

Inadequate medical records and poor patient memory are pronounced among the uneducated, the indigent, the homeless, the drug-addicted, and the criminal elements of society. These patients accordingly present accentuated risks of medical malpractice on the part of medical personnel who engage in post-implantation therapy procedures without adequate information about the implanted medical devices of such patients or even refrain from therapy procedures when such information is unavailable.

Accordingly, a need exists for identifying or otherwise deriving data characterizing an implantable medical device independently of medical records or of the memory of the patient in the body of which that device is implanted. Ideally, this should be able to be accomplished without directly accessing the medical device or prematurely exposing it to the environment exterior to the body of the patient.

Product liability implications of implantable medical devices also suggest a need to be able to identify such devices after their installation in the body of a patient or to derive other characterizing data relative thereof.

It has been suggested by the United States Food and Drug Administration that the manufacturers of implantable medical devices track those devices in order to be able to assist in recalling any that are discovered after the implantation thereof to be defective or to have dangerous effects. Recent publicity related to the failure of artificial breast implants provides but one example of the type of situation lending impetus to some form of medical implant identification and characterization system.

While efforts can be made to track the locations of implanted medical devices through the pooling of information by doctors and medical institutions, this approach can not be expected to be fully effective. Pooled medical information will not identify the physical location of each and every implant recipient. Such individuals will frequently move from one location to another without notifying medical institutions, or treating doctors.

Accordingly, as an additional safety net in this regard it would be desirable to provide all implanted medical devices with some form of identification or characterization data that travels with the patient, is not dependent upon the memory or communication capacities thereof, and can be obtained or accessed nonintrusively at any medical institution from outside the body of the patient.

Nevertheless, to date implants about which characterizing data can be derived after the implantation thereof in a body of a patient are limited to nonpassive implanted devices, which include a self-contained source of electric power. Many of the implantable devices requiring identification or other characterizing data are, however, are too small or inexpensive to warrant the inclusion of active electronic components and self-contained power sources therefor. In addition, the implantation of any such power source in the body of a patient is cause for a heightened regulatory concern relative thereto. This in turn requires substantial time for regulatory approval before the associated device can be put to human use. This in turn causes the device to be more costly then would otherwise be necessary.

OBJECTS AND SUMMARY OF THE INVENTION

Accordingly, one object of the present invention is a system for identifying or otherwise obtaining characterizing data about a medical device implanted in the body of a patient without any reliance whatsoever on the medical records of the patient or the memory or communication capacities thereof.

Yet another object of the present invention is a system such as described above in which the characterizing data required for operation of the system travels with the patient from one institution of post-implantation therapy to another.

Yet another objective of the present invention is a system as described above which does not require intrusive access to an implanted medical device or a resort to radiographic imaging techniques in order to secure characterizing data relative thereto.

Another object of the present invention is a system as described above which is more precise and reliable than palpation or radiographic viewing.

It is another object of the present invention to provide a system for distinguishing between differing medical devices implantable at the same implant location.

Yet another object of the present invention is to provide ready and accurate knowledge to medical personnel of the nature of an implanted medical device, thereby to enable same to undertake proper post-implantation procedures using correct medication and correspondingly proper access tools where such are required.

It is another object of the present invention to provide a system for assisting in the detecting, characterization, and long-term tracking of implanted medical devices.

An additional object of the present invention is to provide such a system as described above which can be utilized in the field without transporting a patient to locations at which massive equipment, such as radiographic viewing equipment can be afforded.

Still an additional object of the present invention is a system as described above that eliminates delay in elementing uncertainty as to the nature of implanted medical devices caused by the consumption of time in location and obtaining copies of medical records.

It is an object of the present invention to provide a plurality of different types of implantable medical devices that can supply to medical personnel post-implantation data relative thereto.

Yet another object of the present invention is to reduce unequal barriers to effective post-implantation treatment imposed on patients disadvantaged by age, mental infirmity, languages differences, drug addiction, and severe disease.

Another object of the present invention is a system as described that does not rely on written or computerized patent medical records for characterizing data about an implanted medical device.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a system is provided for electronically acquiring from outside the body of a patient data pertaining to a medical device implanted therein. The system comprises three (3) elements: the implantable medical device, a hand-held characterization probe for use external to the body of the patient at the implant location associated with the medical device, and a characterization tag containing data about the device that is secured thereto before implantation. The characterization tag is activated by the probe through the skin of the patient, thereby to communicate to the characterization probe the data stored in the characterization tag pertaining to the medical device.

The characterization tag of the present invention may comprise, for example, a structural substrate and a field detecting coil mounted thereto. The field detecting coil is capable of inductively coupling with an alternating magnetic field generated external to the body of the patient. By absorbing energy from that alternating magnetic field the field detecting coil generates a detecting coil signal.

The characterization tag further comprises a coding means secured to the substrate and electrically coupled to the field detecting coil. The coding means selectively loads and unloads the field detecting coil in a predetermined sequence of loading conditions when the detecting coil signal is generated. The sequence of loading conditions corresponds to the data pertaining to the medical device stored in the characterization tag. The loading and unloading of the field detecting coil varies the amount of energy absorbed from the alternating magnetic field in generating the detecting coil signal.

Typically, the alternating magnetic field in the system of the present is produced by a field generating coil disposed in the housing of the characterization probe, the field generating coil is coupleable to a source of alternating electric power to produce the alternating magnetic field. Coupled to the field-generating coil is a sensor means that produces a probe signal reflecting variations in the amount of the energy absorbed from the alternating magnetic field by the characterization tag on the implanted medical device. A digital decoding means is coupled to the sensor means for processing the probe signal to produce a digital data signal that corresponds to variations in the amount of the energy absorbed from the alternating magnetic field by the implanted medical device. Thereafter the digital decoding means correlates those variations with data pertaining to the medical device, and is able to advise a user of the content of that data.

The cooperating physical structures of the field generating and the field detecting coils is of significance. A first capacitor is connected in parallel to the field generating coil, thereby together therewith to comprise a first resonant circuit that is housed in the hand-held identification probe. A first resonant frequency is associated with that first resonant circuit. Correspondingly a second capacitor is connected in parallel to the field detecting coil, thereby to comprise a second resonant circuit having associated therewith a second resonant frequency. The second resonant frequency is substantially equal to the first resonant frequency of the first resonant circuit.

In the physical configuration of the characterization tag, the substrate, the field detecting coil, and the coding means and encapsulated in a moisture-proof, biocompatible material. The characterization tag can assume an elongate or an disc-type configuration. Either maybe disposed in a characterization tag recess formed in a surface of the medical device or, where the medical device is comprised of a plurality of components, secured between a pair of such components prior to the assembly thereof.

Numerous medical devices can benefit from the use of the inventive system.

One such medical device comprises an implantable access port. In the most generalized form thereof, the access port comprises a needle-impenetrable housing enclosing a first fluid cavity and defining a first access aperture through the housing that communicates with the first fluid cavity. A needle-penetrable septum is captured by the housing sealing the first access aperture.

Where the housing of the access port is a unitary structure, or where it is otherwise desirable to do so, a characterization tag recess is formed on the exterior of the housing, and the characterization tag is retained in that characterization tag recess by a biocompatible potting material. Alternatively, where the housing comprises a plurality of components, the characterization tag may be permanently captured between a pair of those components.

Such components in an access port may comprise a base having a flat floor and walls normal and upstanding therefrom which define the first fluid cavity, and a cap configured to receive the base. The cap itself comprises a top wall having formed therethrough the first access aperture at such a position as is opposite the first fluid cavity when the base is received in the cap. A skirt depends from the periphery of the top wall to enclose the walls of the base when the cap is received therein.

Alternatively, the housing of the access port can enclose a second fluid cavity and define a second aperture communicating through the housing with the second fluid cavity. The inventive characterization tag can be disposed either in a characterization tag recess on the exterior of such a housing or be permanently captured between a pair of components of which the housing is comprised.

Typically such components may comprise a base as described previously, but which defines a second as well as a first fluid cavity, a planar septum support configured to mate with the ends of the walls of the base opposite floor thereof, and a cap configured to receive the septum support and the base. Formed through the septum support are first and second septum receiving apertures each positioned above a respective fluid cavity when the planar septum support mates with the base. First and second needle-penetrable septums are captured between the cap and the septum support sealing the septum receiving apertures.

Alternatively, a medical device benefitting from the inventive system can comprise an implantable access port that lacks any fluid cavity or needle-penetrable septum whatsoever. This type of access port may comprise a needle-impenetrable housing enclosing and defining a plurality of spaces. These spaces include a valve chamber, an outlet passageway communicating between the valve chamber and the exterior of the housing, and a non-linear entry passageway communicating at a distal end thereof with the valve chamber and a proximal end thereof with the exterior of the housing. A funnel-shaped entrance orifice is formed in the surface of the housing communicating at the narrow end thereof with the entry passageway. A leaflet valve is captured by the housing in the valve chamber, thereby to provide a selectively-openable fluid seal between the entry passageway and the outlet passageway.

As before, a characterization tag recess can be formed on the exterior of the housing with the characterization tag retained therein by a biocompatible material, or the characterization tag can be permanently captured between a pair of any components of which the housing is comprised.

By way of example, such components can comprise a needle-impenetrable body portion defining therewithin the valve chamber, the entry passageway, the entrance orifice, and an access aperture that communicates through the housing with the valve chamber on the side of the valve chamber opposite the entry passageway. In cooperation therewith is assembled a valve chamber plug itself defining the outlet passageway and being securable in the access aperture to capture the leaflet valve in the valve chamber.

Alternatively, a suitable medical device with which use of the inventive system is compatible comprises a prosthetic device, such as an implantable hip joint. Typically, such an implantable hip joint comprises a shaft having first and second ends and a cup portion attachable to the hip bone of the patient. The first end of the shaft is attachable to the femur of the patient, while the second end of the shaft terminates in a spherical portion. The cup portion is so configured on the side thereof opposite the hip bone as to pivotally receive the spherical portion of the shaft in a ball-end-socket relationship.

The characterization tag can be secured to the shaft or cup in a characterization tag recess using a biocompatible material or captured between a pair of any components of which the shaft is comprised.

The present invention also contemplates a method for the acquisition from outside the body of the patient of data pertaining to a medical device implanted therein. That method comprises the steps of securing a characterization tag is described above to a medical device, surgically implanting the medical device at a predetermined implant location in the body of a patient, generating an alternating magnetic field external to the body of the patient in the vicinity of the implant location, and sensing variations in the amount of the energy absorbed from the alternating magnetic field by the characterization tag.

That method may further comprise the steps of producing a probe signal reflecting the variations in the amount of energy absorbed from the alternating magnetic field by the characterization tag, processing the probe signal to produce a digital data signal corresponding to the variations in the amount of energy absorbed from the alternating magnet field by the data tag, and correlating the digital data signal with the data pertaining to said medical device. Optimally, the method includes the step of providing a visual indication of the data pertaining to the medical device.

Where the medical device is of a unitary construction or it is otherwise desirable to do so, the step of securing the characterization tag thereto comprises the steps of forming a characterization tag recess in a surface of the medical device and securing the characterization tag in the characterization tag recess utilizing a biocompatible potting material. Otherwise, if the medical device is comprised of a plurality of components, the step of securing the characterization tag thereto can comprise the steps of assembling the medical device from that plurality of components and permanently capturing the characterization tag between a pair of those components.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 18 is an cross-sectional elevation view of the implantable access port illustrated in FIG. 17 taken along section line 18—18 shown therein;

FIG. 19 is an exploded perspective view of the components of the implantable access port illustrated in FIGS. 17 and 18;

DESCRIPTION OF THE PREFERRED EMBODIMENT

Figure 1:
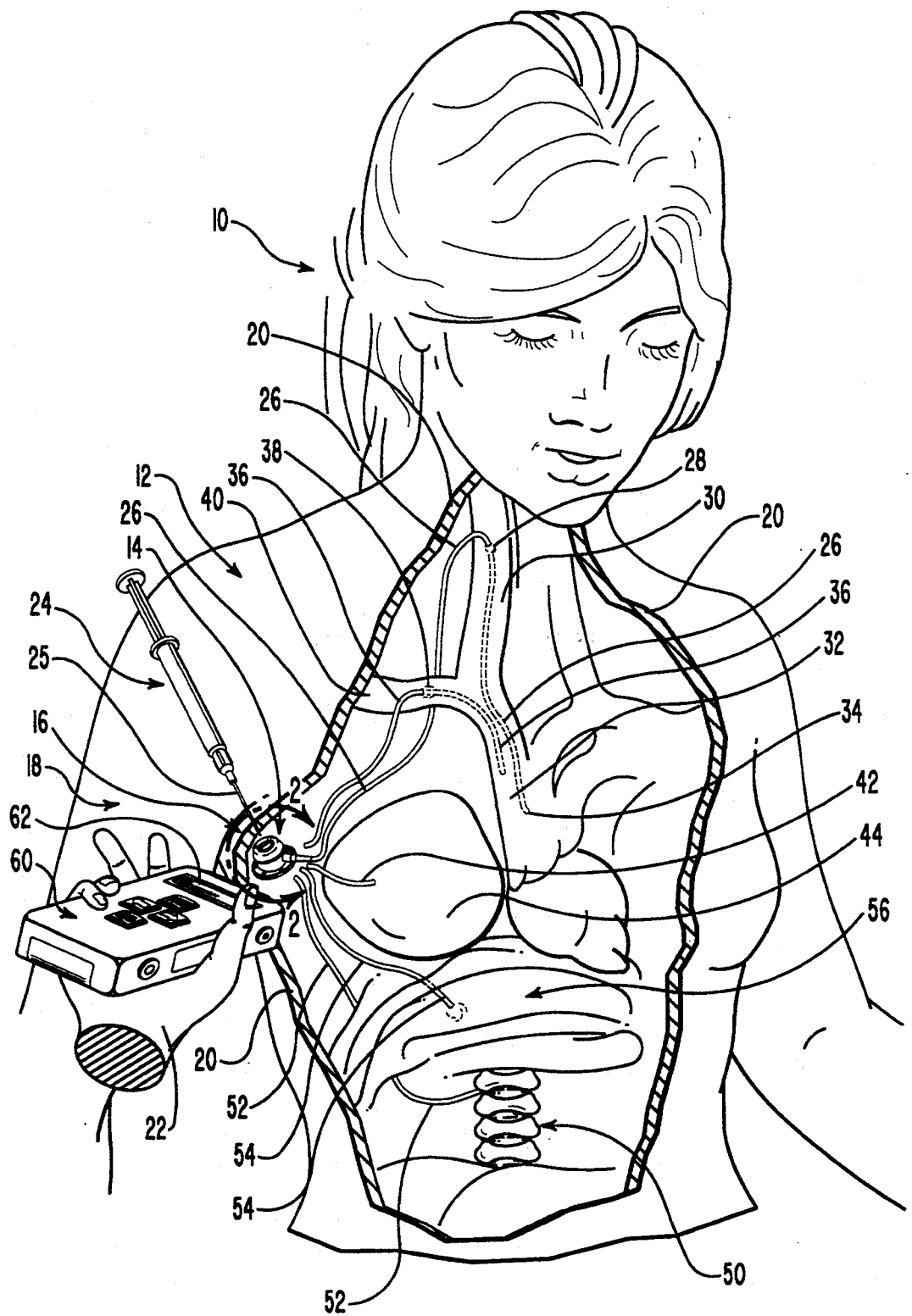
FIG. 1 is a perspective view of the elements of one embodiment of the inventive system for permitting the acquisition from outside the body of a patient of data pertaining to a medical device shown implanted therein.

FIG. 1 illustrates an environment in which the system of the present invention finds utility. There a patient 10 is shown having a body 12 into which a medical device 14 had previously been installed at an implant location 16 in the right chest, forward of and below the arm 18 of patient 10. Thus, medical device 14 is hidden from direct view by the skin 20 of patient 10 that covers implant location 16. Visual observation cannot, therefore, be utilized to identify or derive other characterizing data about medical device 14.

Implant location 16, and thus the position of medical device 14 within body 12 of patient 10, can in many instances be ascertained through palpation of skin 20 of patient 10 by the hand 22 of a medical attendant. Nevertheless, this manner of interacting with medical device 14 will also fail to identify medical device 14 with any degree of certainty or to derive therefrom any other characterizing data useful to the medical attendant. As implant location 16 in the right chest of body 12 of patient 10 is a preferred implant location for numerous medical devices, the medical attendant for patient 10 cannot independently verify the nature of medical device 14, so as to adopt correct therapeutic procedures relative thereto.

In order to illustrate the advantages of the inventive system in avoiding certain medical risks attendant to post-implantation therapeutic procedures, skin 20 of patient 10 has been broken away in FIG. 1 to reveal several significant internal anatomical features in the chest and neck of patient 10, as well as the nature of medical device 14.

Accordingly, from FIG. 1 it can be appreciated that medical device 14 comprises an implantable access port of a type to be disclosed subsequently in greater detail. Basically the access port includes a needle impenetrable housing that encloses a fluid cavity and defines an access aperture through the housing that communicates with the fluid cavity. A needle-penetrable septum is captured in the access aperture sealing the fluid cavity.

Medicament placed in the fluid cavity of medical device 14 is communicated therefrom to any of a plurality of possible locations in body 12 of patient 10 by an associated catheter secured to a hollow outlet stem on medical device 14 which communicates with the fluid cavity. As such catheters cannot be located by palpation, the identity and purpose of medical device 14 cannot be ascertained by palpation alone.

It would be imprudent for the medical attendant of patient 10 to proceed with therapeutic activity relative to medical device 14 without further knowledge about medical device 14. For that knowledge the medical attendant should not rely upon the knowledge of patient 10. If medical records for patient 10 are not on hand, or have not been kept current with regard to medical device 14, then therapeutic procedures, however urgent, will have of necessity to be foregone.

An access tool 24 corresponding an access port such as medical device 14, must be utilized to penetrate skin 20 of patient 10 and interact with medical device 14. Nevertheless, without adequate information regarding the nature of medical device 14 or the disposition of the catheter utilized therewith, the correct type and size of access tool 24 to be used therewith cannot be known. While access tool 24 is shown in the form of a hypodermic syringe, having a non-coring needle 25, certain access ports require in lieu thereof, the use of a semi-rigged catheter inserted through skin 20 of patient 10 on a needle used without any syringe.

Access tool 24, like medical device 14, is thus shown in FIG. 1 by way of illustration of classes of each respective medical device which could be involved in the case of patient 10.

Even if an appropriate type of access tool 24 does happen to be utilized by the medical attendant of patient 10, it is the location of the distal tip of the catheter implanted with associated medical device 14 that will determine the proper type of infusate to be injected the fluid cavity in the housing of medical device 14. In FIG. 1 a plurality of catheters are illustrated extending from medical device 14 by various routes to several alternate treatment sites in body 12 of patient 10.

One of these, catheter 26, is shown actually attached to medical device 14. Catheter 26 extends through body 12 of patient 10 to a puncture site 28 in the right inner jugular vein 30 of patient 10, where catheter 26 enters the cardiovascular system of patient 10 and extends there through to vena cava 32. There medicament from distal end 34 of catheter 26 can be introduced into the blood of patient 10 in region of high-volume flow and turbulence.

Nevertheless, these facts regarding the catheter associated with medical device 14, and even other characterizing data about medical device 14, would not normally be available to the medical attendant for patient 10 absence the ability to make reference to the medical files pertaining thereto.

Alternately, the catheter utilized with medical device 14 might like catheter 36 illustrated in FIG. 1 extend to vena cava 32 of patient 10 but by an alternate route, entering the cardiovascular system of patient 10 at a puncture site 38 in the right subclavian vein 40 thereof. In all likelihood, the same medicament would be injected by access tool 24 into the fluid cavity in the housing of medical device 14, were either catheter 26 or catheter 36 were attached thereto.

This would not, however, be the case, if the catheter utilized with medical device 14 where one of the other catheters illustrated in FIG. 1. For example, medical device 14 might be coupled by way of a catheter to a tissue expander 44 implanted in the breast of patient 10 for the purpose of gradually enlarging a recess into which eventually to install an artificial breast implant. While chemotherapeutic medicaments would typically be injected into medical device 14, if catheters such as catheters 26, 36 were secured thereto, the purpose of medical device 14 with catheter 42 attached thereto is radically different. The injection of chemotherapeutic medicaments into tissue expander 44 could possibly destroy that device or interact adversely with chemicals already disposed therein. If tissue expander 44 were ruptured, chemicals would leak therefrom into body 12 of patient 10, and even further consequential injury would result.

Alternatively, medical device 14 might have been installed in body 12 of patient 10 for the purpose of routinely providing anesthesia to the epidural space located in the spine 50 of patient 10. A catheter 52 useable with medical device 14 toward that end is also illustrated in FIG. 1. The injection of chemotherapeutic medicaments through medical device 14, as if medical device 14 were being utilized with a catheter such as catheter 26 or catheter 36, would be disastrous in the case of medical device, such as medical device 14 connected to catheter 52.

Finally, by way of illustration of the wide variety of therapeutic procedures that could be conducted from a medical device installed at implant location 16, FIG. 1 illustrates another catheter 54 which could be coupled to medical device 14 in order to permit routine administration of antibiotics and other selected solutions to the peritoneal cavity of patient 10 located below diaphragm 56. Again, infusion of incorrect medicaments at this location would not only thwart the desired therapy, but many instances would cause additional bodily injury.

Nevertheless, through use of a system, such as that provided by the present invention for permitting the acquisition of data from outside the body of a patient pertaining to medical devices implanted therein, the medial attendant for patient 10 can become fully apprised of relevant data pertaining to medical device 14 in order to practice appropriate, risk-free therapeutic procedures relative thereto. In the most general form thereof, the system of the present invention comprises three elements, two of which are readily discernable in FIG. 1, and the other of which will be disclosed subsequently in detail. That system includes naturally medical device 14 and in addition thereto a characterization tag not shown in FIG. 1 which is secured to medical device 14 prior to the implantation thereof. The characterization tag carries therein electronic data pertaining to medical device 14 which is recoverable from outside body 12 of patient 10, by the third element of the inventive system, a medical device characterization probe 60 shown in FIG. 1 in hand 22 of a medical attendant in the vicinity of implant location 16. Characterization probe 60 is capable of interacting with the characterization tag attached to medical device 14 to obtain therefrom the data stored therein pertaining to medical device 14. That information is displayed on screen 60 of characterization probe 60 for the benefit of the medical attendant of patient 10. The entire process can be accomplished without penetrating skin 20 of patient 10, and without recourse to the memory or the medical records thereof.

Immediately below a plurality of embodiments, both of a characterization tag incorporating teachings of the present invention and of characterization probe 60 will be discussed. Thereafter, several implantable medical devices worthy of benefiting from the inventive system will be disclosed. Finally, bearing in mind that the inventive system and method each comprise the combination described above, reference will be made to one known detailed embodiment of electronic technology adaptable toward the ends for use in the environment of the present invention.

Figure 2:
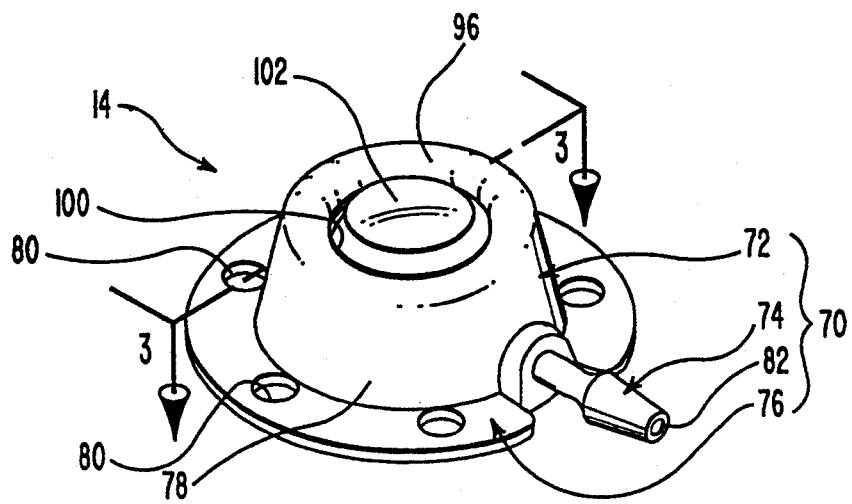
FIG. 2 is an enlarged prospective view of the implanted medical device illustrated in the system shown in FIG. 1.

Accordingly, FIG. 2 illustrates an enlarged perspective view of medical device 14 without catheter 26 of FIG. 1 attached thereto. As readily appreciated there, medical device 14 comprises a needle-impenetrable housing 70 itself including three elements. These are a body portion 72, an outlet stem 74, and a suture flange 76 encircling the base 78 of body portion 72. Apertures 80 formed through suture flange 76 permit the surgical securement of medical device 14 at implant location 16. Outlet stem 74 encloses an outlet passageway 82 which communicates with a fluid cavity defined internal to body portion 72. The proximate end of catheter 26 shown in FIG. 1 is advanced over the exterior of outlet stem 74 in order to secure catheter 26 to medical device 14 and to permit the fluid cavity within body portion 72 to communicate by way of catheter 26 with distal end 34 thereof. Naturally, for medical device 14 to be used for an alternative purpose, outlet stem 74 of medical device 14 would be coupled in a similar manner to any number of alternate catheters, such as catheters 36, 42, 52, or 54 shown in FIG. 1.

Figure 3:
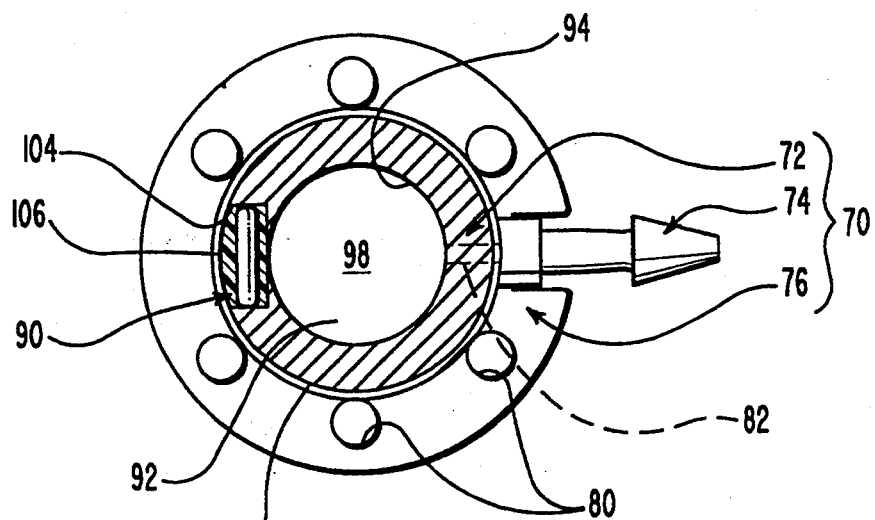
FIG. 3 is a cross-sectional plan view of the implanted medical device illustrated in FIG. 2 taken along section line 3—3 shown therein and illustrating a characterization tag incorporating teachings of the present invention secured in a characterization tag recess on the exterior thereof.

FIG. 3 illustrates the internal structure of medical device 14, as well as a characterization tag 90 as described in general terms previously being attached thereto. FIG. 3 illustrates that housing 70 of medical device 14 comprises a generally flat floor 92 and sidewalls 94 extending from the periphery of floor 92 to the periphery of a top wall 96 of housing 70 shown in FIG. 2. Floor 92, sidewalls 94, and the interior surface of top wall 96, therefore, define a fluid cavity 98 within housing 70. Outlet passageway 82 in outlet stem 74 communicates with fluid cavity 98 as shown. Formed through top wall 96 of housing 70 is a first access aperture 100 in which is captured a needle-penetrable septum 102 which seals first access aperture 100. Fluid cavity 98 is intended to be accessed by the penetration of septum 102 with needle 25 of an appropriate access tool, such as access tool 24 shown in FIG. 1. Nevertheless, the medical attendant of patient 10 cannot know this fact, or undertake correct therapy procedures using proper dosages and proper types of medicament, unless the identity or other characterizing data about medical device 14 is known thereto.

It is the purpose of characterization tag 90 in combination with characterization probe 60 shown in FIG. 1 to provide the medical attendant of patient 10 with such data. It should be understood that the type of data available through the use of characterization tag 90 in combination with medical device 14 could include not only data pertaining to the nature and purpose of medical device 14, but also data as to the manufacturer, composition, size, date of installation, purpose of use, and the nature of other associated or attached devices, such as catheter 26.

As medical device 14 illustrated in FIGS. 1–3 is of a unitary construction, characterization tag 90 is disposed in a characterization tag recess 104 formed on the exterior of housing 70. Characterization tag 90 is then retained in characterization tag recess 104 by use of a biocompatible potting material 106, such as an ultraviolet adhesive or a cyanoacrylate. This procedure is completed prior to the implantation of medical device 14 at implant location 16 shown on FIG. 1. Alternatively, where a medical device, such as medical device 14 comprises a plurality of components, characterization tag 90 may be permanently captured between a pair of those components prior to the assembly of those components into a medical device. Such a medical device will be disclosed subsequently.

Figure 4:
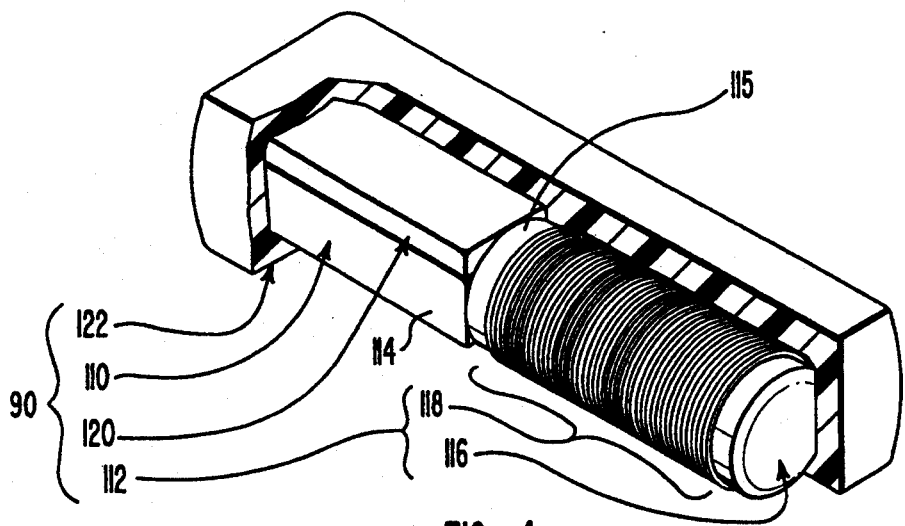
FIG. 4 is a perspective view in partial break away of the characterization tag in FIG. 3.

FIG. 4 is an enlarged perspective view of characterization tag 90 initially illustrated in FIG. 3. As seen there, characterization tag 90 comprises a structural substrate 110 upon which the balance of the elements thereof are secured. The first of these additional elements is a field detecting coil 112 mounted at a first end 114 of structural substrate 110. Field detecting coil 112 itself comprises a core 116 and a conductor 118 wrapped about core 116. Field detecting coil 112 is attached to first end 114 of structural substrate 110 by securing a first end 115 of core 116 thereto using a suitable adhesive, such as an epoxy.

Field detecting coil 112 is capable of inductively coupling with an alternating magnetic field generated external to body 12 of patient 10 and thereby of generating a detecting coil signal through the mechanism of absorbing energy from that alternating magnetic field. In the system of the present invention, the external alternating magnetic field is produced by characterization probe 60 shown in FIG. 1 in a manner to be disclosed in fuller detail subsequently. Core 116 of field detecting coil 112 can be comprised of a ferrous material in order to enhance the magnetic coupling thereof with the external magnetic field. Nevertheless, the implantation of articles of ferrous material in the body of a patient can cause associated problems when the patient is subjected to a strong magnetic field. This would be the case when the patient is diagnosed using a technique such as that of magnetic resonance imaging (MRI). During MRI procedures, implantable articles comprised in whole or in part of ferrous material produce distortions in the MRI image acquired. In addition, however, the result forces on articles of ferrous material can become strong enough to distort, fracture, or even relocate such articles within the body of a patient. Accordingly, core 116 of characterization tag 90 may alternatively be comprised of a non-ferrous material.

Where conductor 118 is wound upon an appropriate mandrill, and that mandrill is removed prior to the assembly of conductor 118 onto structural substrate 110, the core of field detecting coil 112 would in effect be hollow and thus comprised of air or other filler material entered into conductor 118. In such circumstances, the attachment of conductor 118 to structural substrate 110 would be effected by detachment of the leads of conductor 118 only to structural substrate 110.

An additional element of characterization tag 90 illustrated in FIG. 4 is a integrated circuit chip 120 which is secured to structural substrate 110 and electrically coupled to field detecting coil 112, thereby to receive the detecting coil signal generated in field detecting coil 112 by the interaction thereof with an alternating magnetic field. According to one aspect of the present invention, integrated circuit chip 120 includes a coding means for selectively loading and unloading a field detecting coil, such as field detecting coil 112, in a predetermined sequence of loading conditions responsive to the detecting coil signal generated by the field detecting coil. The loading and unloading of a field detecting coil in this manner varies the amount of energy absorbed from any alternating magnetic field coupled to the field detecting coil in generating the detecting coil signal.

In this manner, data pertaining to medical device 14, that is stored in the coding means of integrated circuit chip 120 is detectible remote from medical device 14 and particularly external to body 12 of patient 10, by appropriate electrical circuitry carried, for example, in a device, such as characterization probe 60 illustrated in FIG. 1. In effect, that circuitry detects variations in the amount of energy absorbed from the alternating magnetic field by the field detecting coil and the coding means together.

In this light, field detecting coil 112 and integrated circuit chip 120 comprise components of a medical device data circuit that is secured to medical device 14 prior to the implantation thereof. The data circuit is powered by energy absorbed through the mutual inductive coupling thereof with an alternating magnetic field generated external to the body of the patient.

An additional element of such a medical device data circuit is a capacitor connected in parallel to field detecting coil 112. In the embodiment of characterization tag 90 illustrated in FIG. 4, such a capacitor can take the form of structural substrate 110. Together that capacitor with field detecting coil 112 define a resonant circuit secured to medical device 14 and having associated therewith a corresponding resonant frequency. Optimally the resonant frequency of the resonant circuit secured to medical device 14 is substantially equivalent to the frequency of the alternating magnetic field generated external to body 12 of patient 10 in characterization probe 60 for the purpose of interacting with characterization tag 90.

In FIG. 4, the above-described components of characterization tag 90 are shown encapsulated in a moisture proof biocompatible coding 122. Coding 122 may comprise a Parylene ™ coating such as that available through commercial sources. Alternatively, coding 122 may comprise an ultraviolet adhesive, a cyanoacrylate, or glass. Where a Parylene ™ coating is utilized, it may be in addition encased by an ultraviolet adhesive or by a cyanoacrylate.

As illustrated in FIG. 4, characterization tag 90 comprises an elongate member having a diameter less than or equal to approximately 2.5 millimeters and a length less than or equal to approximately 6.0 millimeters. This size of a characterization tag 90 has been found to be sufficiently small to be utilized in a characterization tag recess on the exterior of a wide variety of implantable medical devices, such as the single fluid cavity access port illustrated in FIGS. 2 and 3 as comprising medical device 14. Both smaller and larger sizes of characterization tags are appropriate in certain circumstances.

Figure 5:
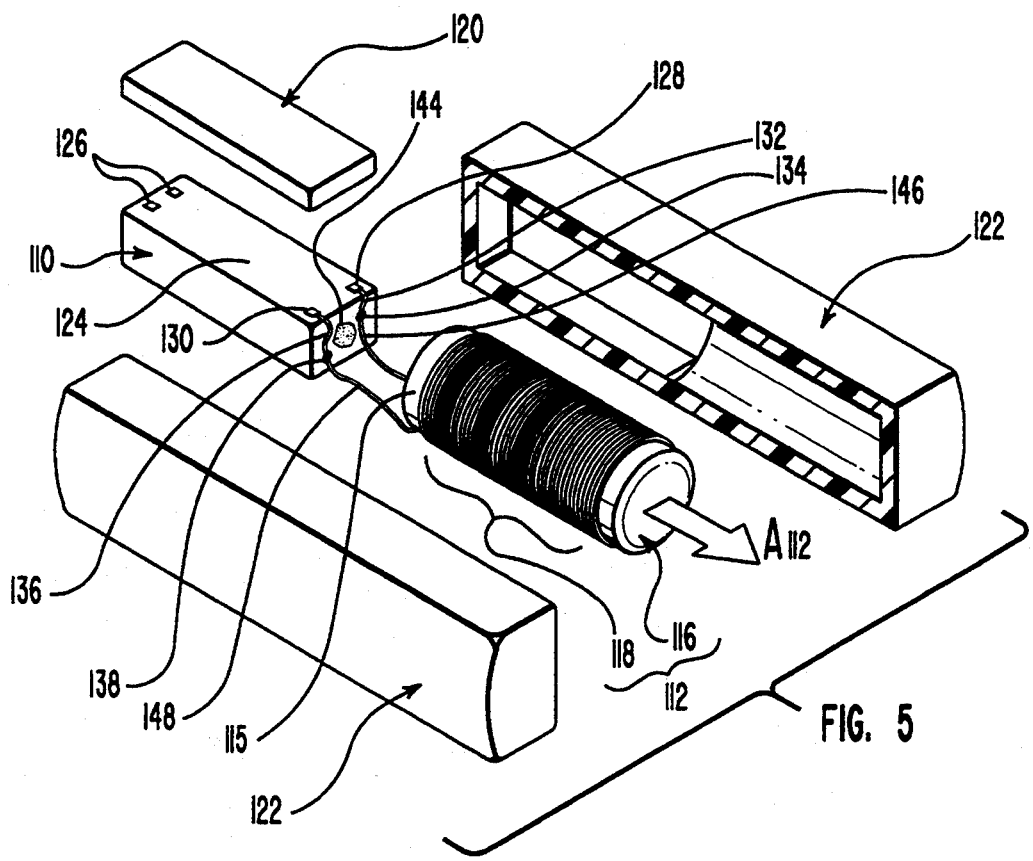
FIG. 5 is an exploded view of the components of the characterization tag illustrated in FIG. 4.

FIG. 5 illustrates the components of characterization tag 90 in a partially disassembled state. There-coating 122 has been severed longitudinally and separated from the balance of the components of characterization tag 90. Integrated circuit chip 120 is illustrated separated from top surface 124 of structural substrate 110 on which are formed inductive integrated circuit chip receiving bumps 126, 128, and 130. Bumps 126 merely form sites for the physical securement of integrated circuit chip 120 to top surface 124 of structural substrate 110. Nevertheless, as structural substrate 110 is comprised of a capacitor, bump 128 is coupled by a lead 132 to a contact 134 on one side of that capacitor. Correspondingly, bump 130 is connected by a lead 136 to a contact 138 on the opposite side of that capacitor.

Both of contact 134, 138 are disposed on a face 140 of structural substrate 110 that opposes and contact first end 115 of core 116 of field detecting coil 112 in the assembled form characterization tag 90 illustrated in FIG. 4. Between contacts 134, 138, a dot of adhesive 144 is illustrated by which first end 115 of core 116 of field detecting coil 112 is secured to structural substrate 110. Also shown in FIG. 5 are leads 146, 148 from conductor 118 of field detecting coil 112. These are electrically coupled, respectively, to contacts 134, 138.

Figure 6:
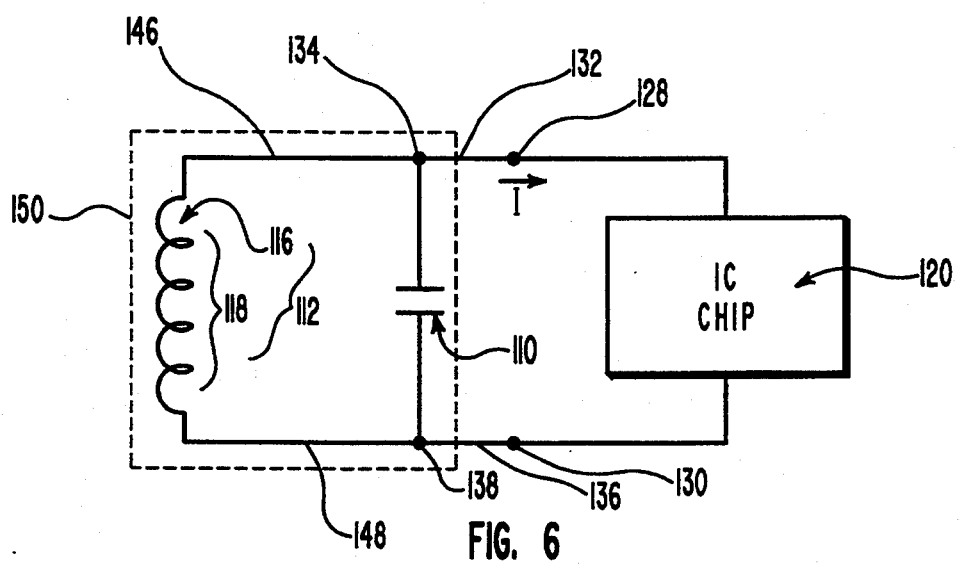
FIG. 6 is a circuit diagram of the electronic components of the characterization tag illustrated in FIGS. 4 and 5.

The resulting interconnections places the capacitor of which structural substrate 110 is comprised in parallel connection to both field detecting coil 112 and to integrated circuit chip 120. These electrical relationships are illustrated in FIG. 6, where electrical elements corresponding to physical elements illustrated in FIG. 5 are identified by reference characters identical thereto. Thus, conductor 118 and core 116, if any, which comprise field detecting coil 112, together with a capacitor in the form of structural substrate 110 define a resonant circuit 150 which is attachable to medical device 14 and has associated therewith a characteristic resonant frequency. Field detecting coil 112 accordingly, couples readily with any alternating magnetic field generated external to body 12 of patient 10 having a frequency closely similar to that of the resonant frequency associated with resonant circuit 150. When thus magnetically coupled to an alternating magnetic field, resonant circuit 150 generates a detecting coil or data circuit signal I through the coding means on integrated circuit chip 120 as shown. It is the function of the coding means to load and unload resonant circuit 150 in a predetermined sequence of loading conditions that correspond to data pertaining to medical device 14. That in turn varies the amount of energy absorbed by field detecting coil 112 from the alternating magnetic field coupled therewith.

One field detecting coil 112 adaptable for the purpose stated utilizes approximately 2750 turns of a number 50 bondable copper conductor 118 on a non-ferrous core 116 to produce a resultant inductance of 1.8 Mh.

By way of reference for future discussion, when a characterization tag, such as characterization tag 90, takes an elongated form, such as shown in FIGS. 4 and 5, the longitudinal axis of the field detecting coil used therewith will for future reference define a field detecting coil axis $A_{112}$ as shown in FIG. 5. The effect of varying the orientation of field detecting coil axis $A_{112}$ to the flux of the alternating magnetic field with which field detecting coil 112 couples will be discussed subsequently.

Figure 7:
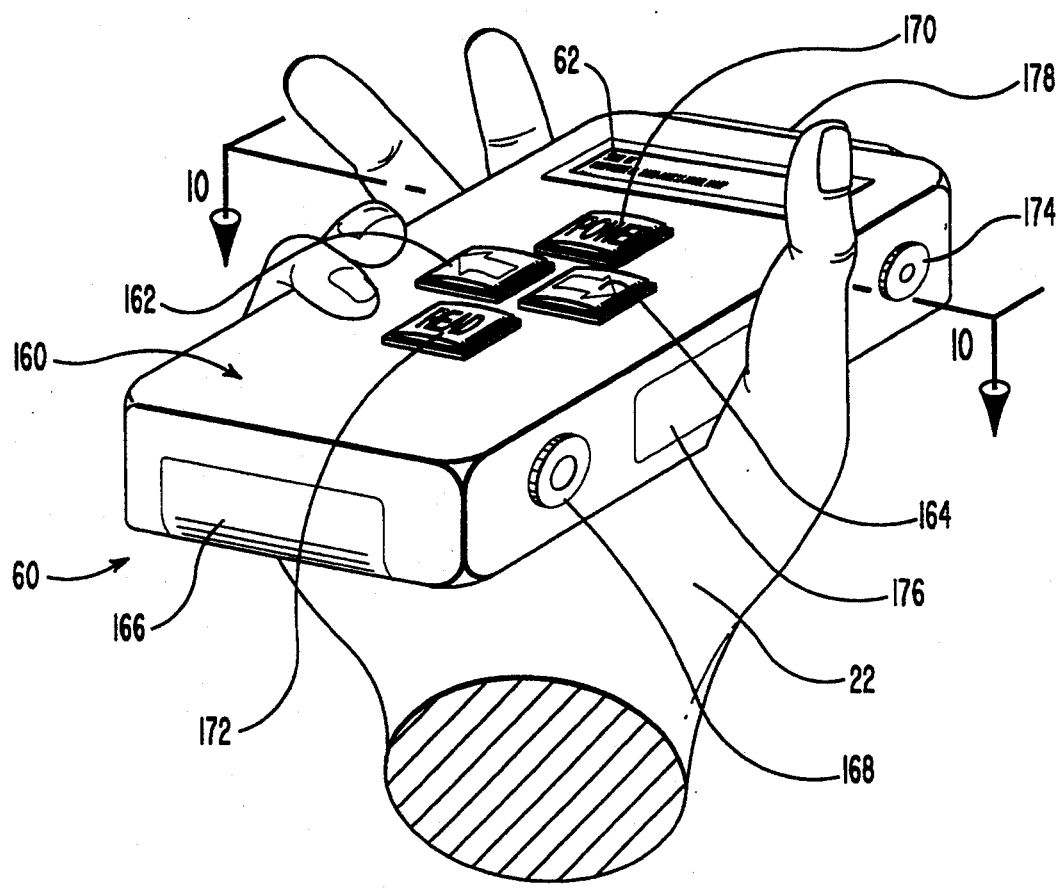
FIG. 7 is a perspective view of the medical device characterization probe illustrated in the inventive system shown in FIG. 1.

FIG. 7 is an enlarged perspective view of characterization probe 60 used to acquire data pertaining to an implanted medical device in the body of a patient from the outside thereof. Characterization probe 60 comprises a hand-held housing 160 movable on the outside of body 12 of patient 10 in the vicinity of implant location 16 for medical device 14. According to one aspect of the present invention, housing 160 encloses field generating means that is coupleable to a source of alternating electric power for generating an alternating magnetic field. Coupled thereto within housing 160 is a sensor means for producing a probe signal reflecting variations in the amount of energy absorbed from that alternating magnetic field by the data circuit or the characterization tag attached to implanted medical device 14.

Also enclosed in housing 160 and coupled to the above-described sensor means is a digital decoding means for performing the dual functions of (1) processing the probe signal to produce a digital data signal corresponding to the variations in the amount of energy absorbed from that alternating magnetic field and (2) correlating those variations with data stored in the data circuit or characterization tag pertaining to the associated medical device.

According to yet another aspect of the present invention, characterization probe 60 includes display means electrically coupled to that digital decoding means and disposed on the exterior of housing 160 for giving a visual indication of data pertaining to implanted medical devices. By way of example and not limitation, characterization probe 60 is shown in FIGS. 1 and 7 as being provided with a display screen 62 capable of providing the medical attendant of patient 10 with a single or a plurality of lines of printed text reflecting that data. Display screen 62 might typically be configured from a liquid crystal display device.

Where characterization probe 60 in combination with characterization tag 90 are together capable of deriving substantial data pertaining to implanted medical device 14, characterization probe 60 according to the teachings of the present invention may comprise means for scrolling the visual indication on display screen 62, thereby to enable a user of the invented system to access data pertaining to implanted medical device 14 that exceeds the display capacity of display screen 62. By way of example and not limitation, toward this end the exterior of housing 160 is provided with a pair of scrolling switches, 162, 164. Scrolling switch 162 advances the text appearing on display screen 26 upwardly, while scrolling switch 164 advances text appearing on display screen 62 downwardly. By this mechanism, the display capacity of the display means of the present invention can be greatly enhanced.

The power for characterization probe 60 may comprise one or more batteries disposed within housing 160 used in combination with a power conversion means coupled thereto for converting direct current into alternating electric power. A door 166 in housing 160 by which to insert and remove such batteries is shown in FIG. 7. Nevertheless, for maximum flexibility characterization probe 60 may also be coupleable to an external source of alternating electric power by means of a receptacle 168 shown on housing 160. When characterization probe 60 is powered by batteries entered into housing 160 through door 166, it is necessary to conserve the expenditure of power thereby.

Accordingly, the exterior of housing 160 of characterization probe 60 is provided with a power switch 170, which provides to the circuitry within housing 160 a minimum amount of power necessary to drive only the digital decoding means of the present invention. A read switch 172 is also provided, which supplies to the field generation means and the sensor means within characterization probe 60 sufficient power to generate the alternating magnetic field with which medical device 14 and characterization tag 90 attached thereto are scanned for the purpose of deriving data therefrom pertaining to medical device 14. Once characterization probe 60 with read switch 172 activated has received from the characterization tag attached to medical device 14 data pertaining to medical device 14, read switch 172 may be deactivated, as characterization probe 60 can function on a reduced level of power to reflect that data on display screen 62.

Optionally, pursuant to the teachings of the present invention, characterization probe 60 may further comprise means to electrically couple the digital decoding means in housing 160 to a computer located external of characterization probe 60. As shown by way of example, and not limitation, housing 160 of characterization probe 60 is provided with a data receptacle 174 by which data can be downloaded from characterization probe 60 to the memory of a larger computer. By this mechanism, information from a plurality of probes, such as characterization probe 60, can be readily pooled in a single large data-base.

Finally, the characterization probe of the present invention may be further provided with upgrade means for revising information in the digital decoding means within housing 60. As shown by way of example and not limitation, housing 160 includes a selectively openable access portal 176. Modular means within housing 160 permits the non-destructive removal and replacement through access portal 176 of all or selected components of the digital decoding means of the present invention. In this manner, the information stored in the digital decoding means relative to potential implantable medical devices, which may be scanned by characterization probe 60 may be updated on a periodic basis as new medical devices bearing characterization tags are developed and marketed. Alternatively, where the digital decoding means within housing 160 is programmable from an external source, the function of the upgrade means of the present invention can be effected through a data receptacle, such as data receptacle 174.

The end of housing 160 opposite from door 166 is provided with a scanning window 178 through which the alternating magnetic field generated by characterization probe 60 can pass unimpeded into body 12 of patient 10 during scanning.

An appropriate characterization probe 60 utilizable in the context of the inventive system comprises a housing 160 having a length that is less than or equal to approximately 6.0 inches. Correspondingly the width of housing 160 may be approximately 3.0 inches and the thickness thereof approximately 1.0 inches. A housing 160 having such dimensions will be easily held in the palm of a medical attendant and will yet be large enough to house conventional sources of battery power and to display sufficient data on display screen 62 as will contribute to the maximum effectiveness of characterization probe 60 and the system in which it finds use.

The field generation means in housing 160 comprises components defining a resonant circuit having associated therewith a corresponding resonant frequency. Such a resonant circuit typically comprises an induction coil, which is electrically coupled to the sensor means of the present invention, and a capacitor connected in parallel to that induction coil. Alternate forms of such field generation means will be disclosed subsequently along with a discussion of the advantages of each form thereof.

Prior thereto, however, a second, disc-like embodiment of a characterization tag 180 utilizable in the system of the present invention will be discussed relative to FIGS. 8 and 9. Like characterization tag 90 illustrated in FIGS. 4 and 5, characterization tag 180 comprises a structural substrate 182 in the form of a disc and a flat field detecting coil 184 mounted on a top surface 186 thereof. Field detecting coil 184 is comprised of the windings of a conductor 188, the opposite ends of which are electrically coupled to structural substrate 182 at contacts 190, 192.

Characterization tag 180 also includes an integrated circuit chip 194 containing a coding means as described earlier relative to characterization tag 90. A biocompatible coating 196 similar to coating 122 utilized in characterization tag 90 encloses characterization tag 180. As with structural substrate 110 of characterization tag 90, structural substrate 182 of characterization tag 180 may advantageously be comprised of a capacitor connected in parallel to field detecting coil 184. The interconnection of the circuitry in integrated circuit chip 194 with that capacitor and with field detecting coil 184 can be effected through the use of contact bumps, not shown, these are similar to bumps 126, 128, 130 disclosed relative to characterization tag 90.

Figure 8:
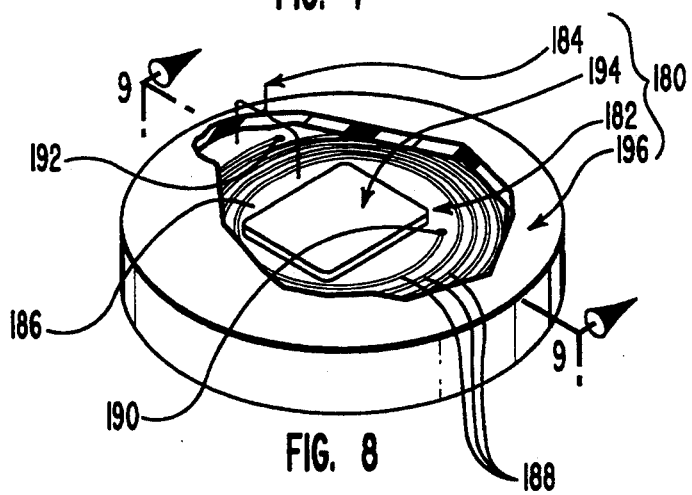
FIG. 8 is a perspective view in partial break away of a second embodiment of a characterization tag incorporating techniques of the present invention.
Figure 9:
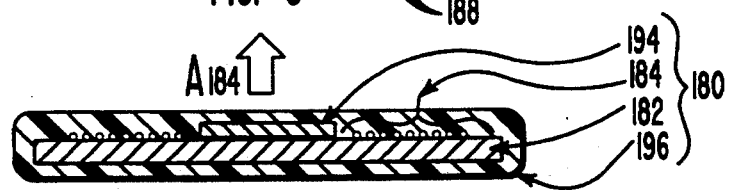
FIG. 9 is a cross sectional elevation view of the characterization tag illustrated in FIG. 8 taken along section line 9—9 shown therein.

In the form illustrated in FIGS. 8 and 9, characterization tag 180 comprises a disc having a thickness less than or equal to approximately 2.5 millimeters and a diameter less than or equal to approximately 20.0 millimeters. A flat field detecting coil 184 comprising approximately 600 turns of number 41 bondable conductor 188 has been used to produce an overall conductance of 4.2 Mh. The outer diameter of such a field detecting coil 184 is approximately 18.0 millimeters, while the inner diameter thereof is approximately 6.0 millimeters.

The utilization of a characterization tag, such as characterization tag 180, in connection with a medical device, such as medical device 14, will be illustrated subsequently. Nevertheless, for convenience of reference in subsequent discussions, it should be observed that field detecting coil 184 contains no core whatsoever. Also field detecting coil 184 defines a field detecting axis A184, which is perpendicular to the plane of field detecting coil 184, defined by top surface 186 of structural substrate 182 at the center of field detecting coil 184.

As discussed above relative to FIG. 7, characterization probe 60 includes field generation means for generating an alternative magnetic field. As shown by way of example in FIG. 10, one embodiment of such a field generating means comprises a field generating coil 198 mounted inside housing 160 at scanning window 178 of characterization probe 60, and being comprised of a core 200 with windings of a conductor 202 thereon. Core 200 assumes a generally elongate shape having a longitudinal axis that is oriented toward skin 20 of patient 10 when characterization probe 60 is moved external to body 12 thereof in the vicinity of an implant location. Core 200 may be comprised of a ferrous material to more effectively direct deeply into body 12 of patient 10 the flux lines 204 of the alternating magnetic field produced by field generating coil from the passage of alternating current through conductor 202.

Alternately, core 200 may be comprised of a non-ferrous material, however. Flux lines 204 extend from both ends of core 200 as shown, but it is the flux lines 204 that penetrate skin 20 of patient 10 that are designed to in the system of the present invention to magnetically couple with a field detecting coil, such as field detecting coils 112, 184 attached to an implantable medical device. A plurality of such field detecting coils disposed at a depth D1 below the surface 206 of skin 20 are shown with the associated field detecting coil axis of each.

Figure 10:
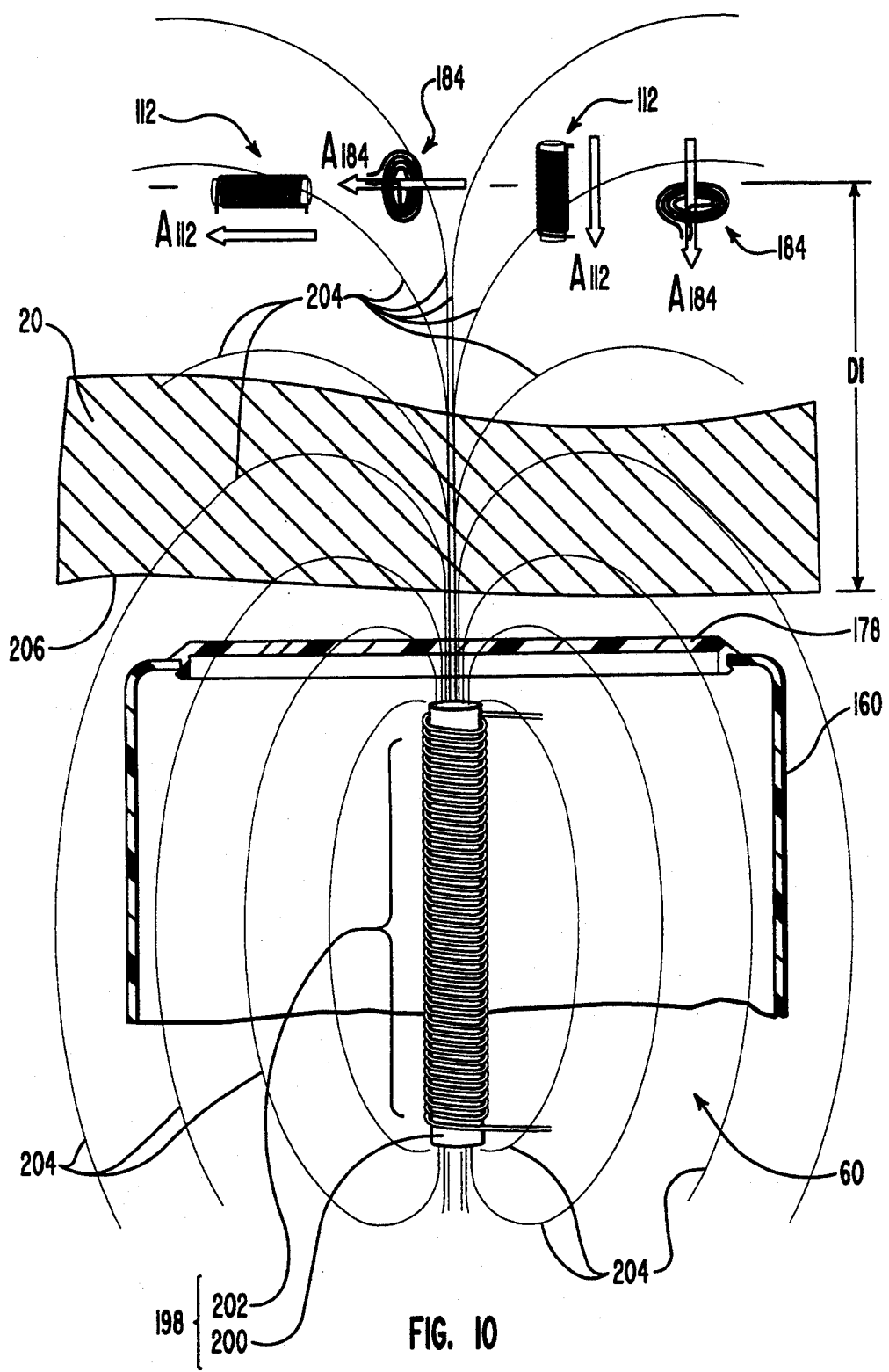
FIG. 10 is a schematic view of a first embodiment of a field generating coil for utilization in the medical device characterization probe shown in FIG. 7 when viewed in the direction of the section line 10—10 shown therein, thereby to illustrate the interaction of that first embodiment of a field generating coil with various orientations and embodiments of field detecting coils used in characterization tags incorporating teachings of the present invention.

Field detecting coils 112, 184 shown on the left side of FIG. 10 have the associated field detecting coil axis of each disposed generally parallel to surface 206 of skin 20, and thus in effect perpendicular to the longitudinal axis of core 200 of field generating coil 198. On the other hand, field detecting coils 112, 184 shown on the right side of FIG. 10 have the field detecting coil axis associated therewith oriented generally perpendicular to surface 206 of skin 20, and thus parallel to the longitudinal axis of core 200.

It has been found that flux lines 204 generated by a field generating coil, such as field generating coil 198, tend to deeply penetrate body 12 and couple to best advantage with field generating coils having the associated field generating coil axis thereof parallel to the surface 206 of skin 20. Thus, field generating coils 112, 184 on the right side of FIG. 10 will couple to the best advantage with the alternating magnetic field generated in characterization probe of FIG. 10.

This is not an indication that alternate orientations of field generating coils have proven inoperable. Rather, the preferred orientation of field detecting coils 112,184 shown on the right side of FIG. 10 permits coupling through the use of less power and therefore facilitates the effective scanning of medical devices implanted at a distance D1 in the body of a patient. The form of characterization tag and the manner and orientation of the attachment of that tag to an implantable medical device will, naturally be highly determinative of the orientation of the corresponding field detecting coil axis relative to the surface of the skin of a patient. Such considerations will in turn influence the type of field generating coil to be used in an inventive system for acquiring data about the medical device from outside the body of the patient.

Figure 11:
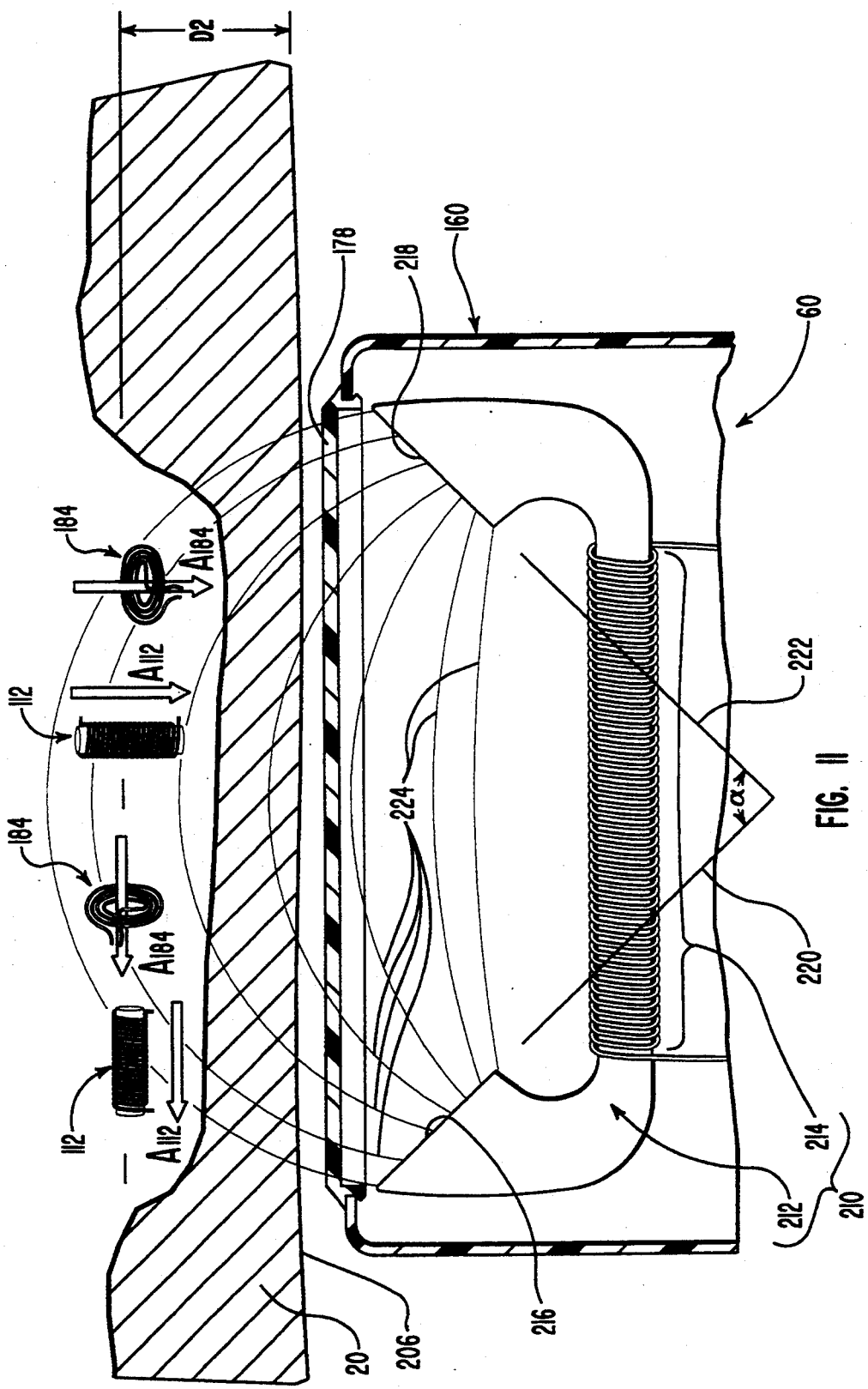
FIG. 11 is a schematic view of a second embodiment of a field generating coil for utilization in the medical device characterization probe shown in FIGS. 7 when viewed in the direction of section line 10—10 shown therein, thereby to illustrate the interaction of that second embodiment of a field generating coil with various orientations and embodiments of field detecting coils used in characterization tags incorporating teachings of the present invention.

An alternate form of a field generating coil 210 utilizable in a characterization probe 60 in the system of the present invention is illustrated in FIG. 11 disposed adjacent scanning window 178 inside housing 160 thereof. Field generating coil 210 can there be seen to comprise a generally C-shaped core 212 and a conductor 214 wrapped about a medial portion thereof. Core 112 terminates at opposite ends thereof in a first flat flux-transmitting surface 216 and a second flat flux-transmitting surface 218.

First flux-transmitting surface 216 defines a corresponding first flux-transmitting plane 220 seen from the edge thereof in FIG. 11. Correspondingly second flux-transmitting surface 218 defines a second flux-transmitting plane 222. First flux-transmitting plane 220 and second flux-transmitting plane 222 form a dihedral angle, the interior of which as shown in FIG. 11 is oriented towards skin 20 of patient 10 when characterization probe 60 is moved external to body 12 thereof in the vicinity of an implant location.

The flux lines 224 of the alternating magnetic field produced by field generating coil 210 when alternating current passes through conductor 214 are shown. The effect of the shape of core 212 of field generating coil 210 and of first and second flux-transmitting surfaces 216, 218 is to produce an alternating magnetic field in which flux lines 204 penetrate skin 20 of patient 10 and pass there through generally parallel to surface 206 thereof.

FIG. 11 illustrates a plurality of field detecting coils disposed at a depth D2 below surface 206 of skin 20 with the field detecting coil axes associated with each. Field generating coils 112, 184 are shown on the left side of FIG. 11 with the field generating coil axes associated therewith being disposed generally parallel to surface 206 of skin 20. Alternatively, field generating coils 112, 184 are shown on the right side of FIG. 11 with the field generating coil axes associated therewith disposed generally perpendicular to surface 206 of skin 20.

Because of the shape of the alternating magnetic field generated by field generating coil 210, it has been found that the distance D2 at which field detecting coils can effectively be disposed below surface 206 of skin 20 of patient 10 is less than the distance D1 shown in FIG. 10. Nevertheless, many implantable medical devices admit of shallow implantation and, accordingly, the configuration of field generating coil 210 is considered to be within the scope of the present invention. Nevertheless, due to the shape of the alternating magnetic field generated by field generating coil 210, a field detecting coil with the field detecting coil axis associated therewith being parallel to surface 206 of skin 20 of a patient, as in the left side of FIG. 11, has been found to produce more effective magnetic coupling than with field generating coils disposed as on the right of FIG. 11 with the field detecting coil axes thereof disposed normal to surface 206 of skin 20.

Figure 12:
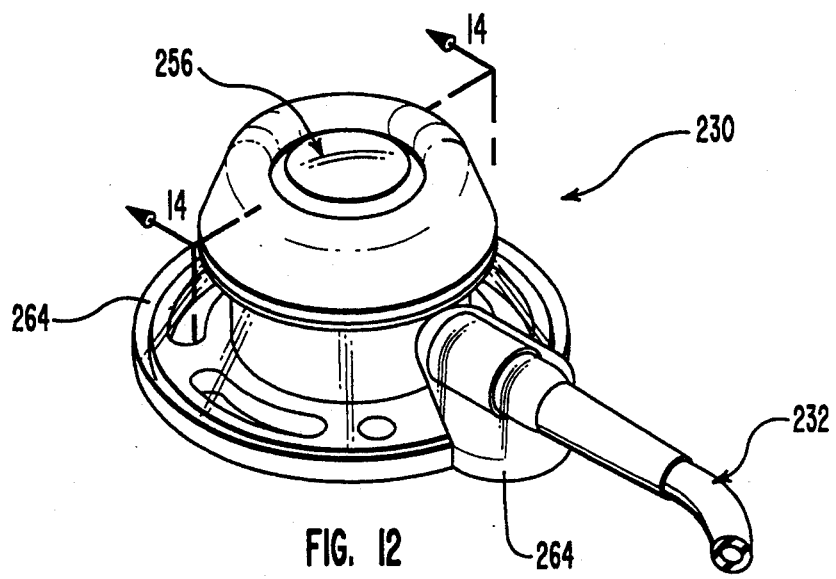
FIG. 12 is a perspective view of a second embodiment of an implantable access port incorporating teachings of the present invention.
Figure 13:
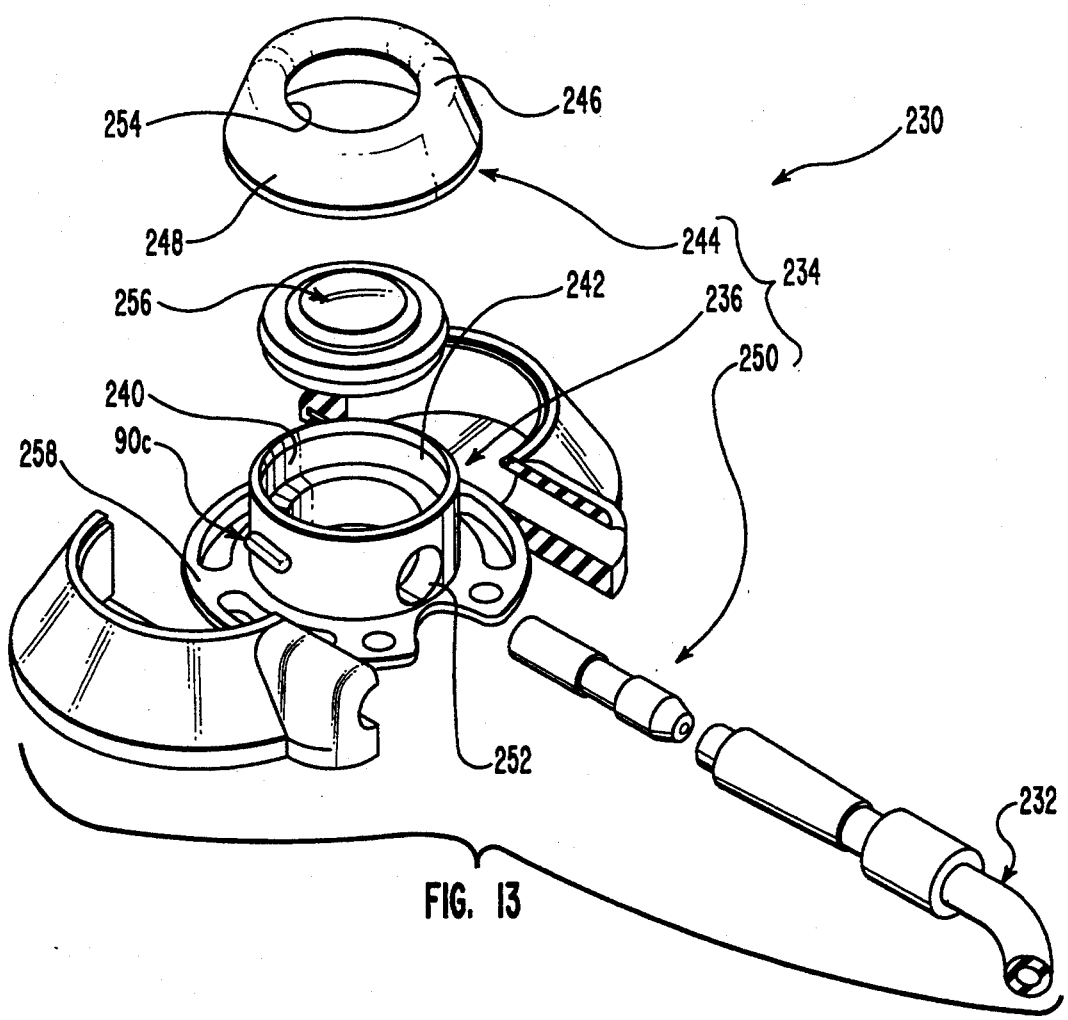
FIG. 13 is an exploded perspective view of the components of implantable access port illustrated in FIG. 12.
Figure 14:
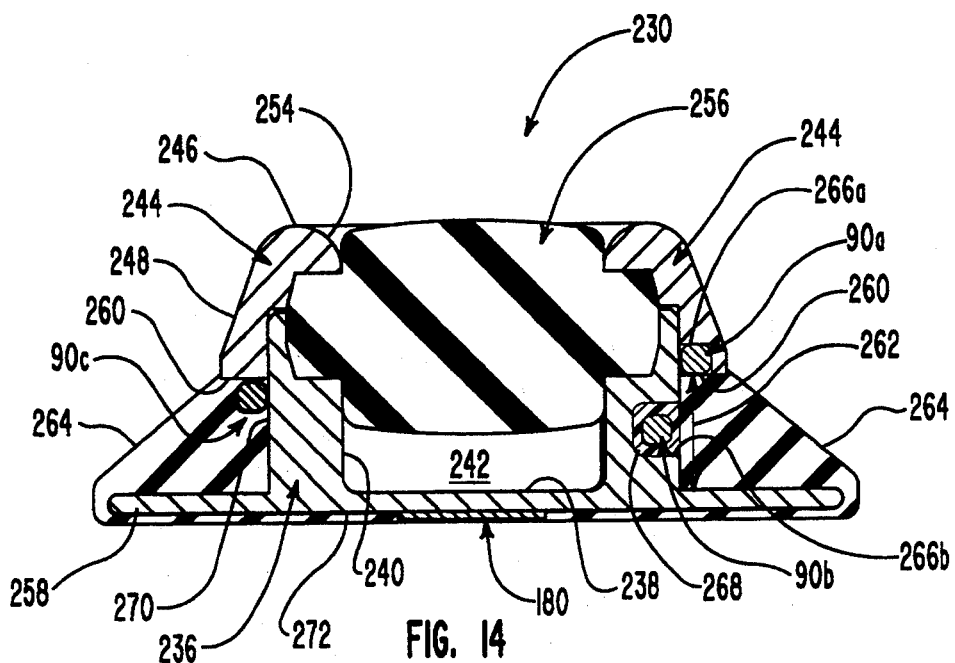
FIG. 14 is a cross-sectional elevation view of the implantable access port of FIG. 12 taken along section line 14—14 shown therein.

FIGS. 12-14 illustrate a second embodiment of an implantable medical device 230 which can incorporate to advantage the teachings of the present invention. Medical device 230 takes the form of a single fluid reservoir infusion port, which is provided to the customer with the catheter 232 associated therewith permanently preconnected thereto. As illustrated in FIG. 13, medical device 230 includes a housing 234 comprised of a base 236 having a flat floor 238 shown to best advantage in FIG. 14 and walls 240 upstanding therefrom to define fluid cavity 242. Housing 234 further comprises a cap 244 having a top wall 246 and a skirt 248 depending therefrom. Lastly, housing 234 comprises an outlet stem 250 configured as an insert for press fitting into an outlet stem receiving aperture 252 formed through wall 240 of base 236.

An access aperture 254 is formed through top wall 246 of cap 244 at a position that is opposite fluid cavity 242 when base 236 and cap 244 have been press fitted or otherwise adhered together. Medical device 230 also includes a needle-penetrable septum 256 that is captured between base 236 and cap 244 to seal access aperture 254, when the components of medical device 230 have been assembled. A suture flange 258 is carried by base 236 of housing 234.

As best appreciated by reference to FIG. 14 when cap 244 and base 236 are assembled, the lower edge 260 of skirt 248 does not meet suture flange 258. Therefore, between lower edge 260 of skirt 248 and suture flange 258 is produced a silicone retaining channel 262 is produced which encircles housing 234 above suture flange 258. Once the components of housing 234 have been assembled, and catheter 232 has been secured to outlet stem 250, the outer portion of housing 234 is embedded in silicone 264.

According to the teachings of the present invention, to permit medical device 230 to provide characterizing data relative thereto to a characterization probe, such as characterization probe 60, a characterization tag is attached to medical device 230. This may be accomplished in a number of different physical configurations best illustrated by reference to FIG. 14.

First, a characterization tag, such as characterization tag 90a can be disposed in a characterization tag recess 266a formed in lower edge 260 of skirt 248 of cap 244. Characterization tag 90a may be retained thereat, either by a biocompatible potting material or by the effect of the imbedment of housing 234 in silicone 264.

Alternatively, a characterization tag, such as characterization tag 90b can be retained in a characterization tag recess 266b by a biocompatible potting material 268 prior to the encapsulation of housing 234 in silicone 264.

Further, after the assembly of the components of housing 234, a characterization tag, such as characterization tag 90c, can be adhered by an appropriate adhesive in the juncture between lower edge 260 of skirt 248 and the outer surface 270 of walls 240. Thereafter housing 234 and characterization tag 90c are embedded in silicone 264.

Yet another alternative for enabling medical device 230 to be utilized in the inventive system is to adhere a disc-shaped characterization tag, such as characterization tag 180 illustrated in FIGS. 7, 8 and 9, to the lower surface 272 of floor 238 of base 236. Thereafter, the encapsulation of housing 234 in silicone 264 will also encapsulate characterization tag 180.

Figure 15:
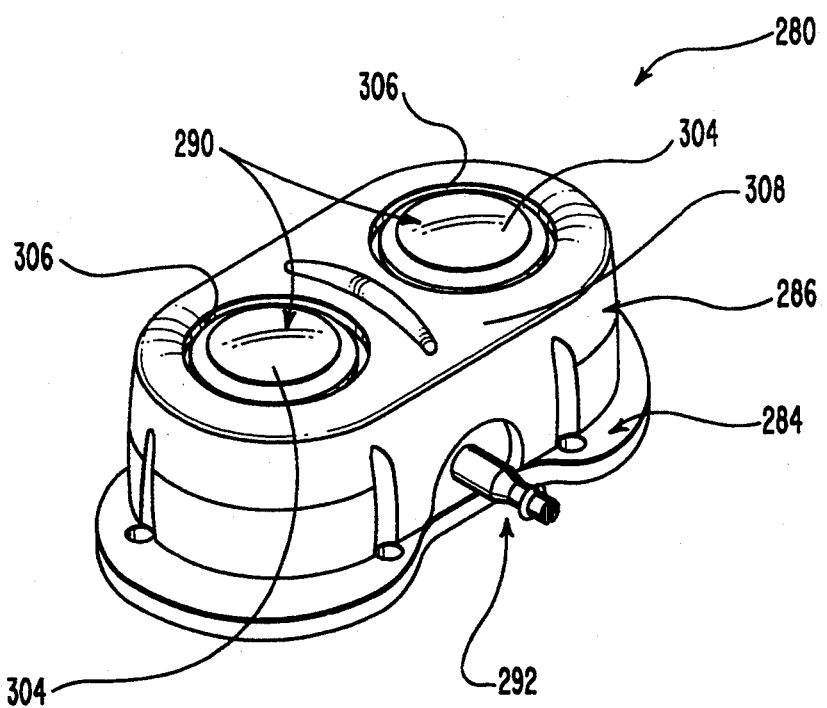
FIG. 15 is a perspective view of a third embodiment of an implantable access port incorporating teachings of the present invention.
Figure 16:
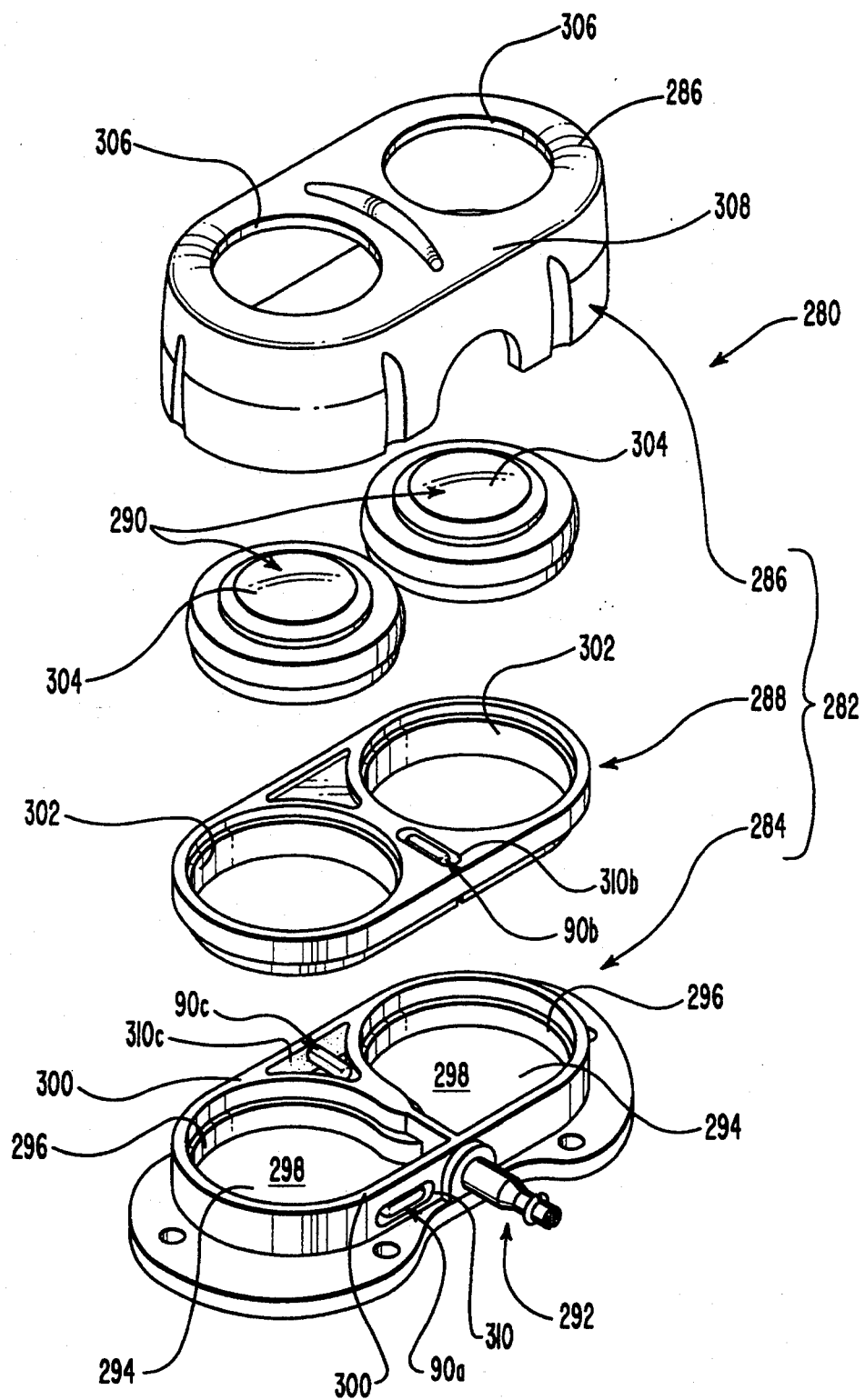
FIG. 16 is an exploded perspective view of the components of the implantable access port illustrated in FIG. 15.

FIGS. 15 and 16 illustrate yet another medical device 280 which can beneficially incorporate teachings of the present invention. Medical device 280 takes the form of a dual-fluid reservoir infusion port comprising a housing 282, which is itself comprised of three usually plastic components that are bonded to each other. Only two of these components, a base 284 and a cap 286 appear in FIG. 15. The third element of housing 282, a septum support 288 appears in FIG. 16.

Medical device 280 also comprises a needle-penetrable septums 290 and an outlet stem 292 by which medical device 280 is coupleable to a dual lumen catheter not shown.

As seen to best advantage in FIG. 16, base 284 has a flat floor 294 and generally curved walls 296 normal to an upstanding therefrom. Walls 296 define a pair of fluid cavities 298. Septum support 288 is assembled to the top 300 of walls 296 and bonded thereto, preferably by ultrasonic welding. Thereafter septums 290 are inserted into septum receiving apertures 302 formed through septum support 288 opposite each of fluid cavities 298. Cap 286 is placed over septum support 288 and walls 296 of base 284 to enclose those structures and capture septums 290 in septum receiving apertures 302. The upper surfaces 304 of septums 290 then protrude through access apertures 306 formed in top wall 308 of cap 286 as shown in FIG. 15.

In order to adapt medical device 280 to use in the inventive system, a characterization tag, such as characterization tag 90 shown in FIGS. 4 and 5 or characterization tag 180 shown in FIGS. 8 and 9, is attached to housing 282. The latter type of characterization tag is not illustrated FIGS. 15 and 16, however.

Nevertheless, as best appreciated by reference to FIG. 16, a characterization tag recess 310a can be formed in a surface of base 284 contacted by cap 286 when housing 282 is assembled. A characterization tag 90a is disposed therein prior to that assembly.

Alternatively, a characterization tag recess 310b can be formed in a surface of septum support 288 contacted by cap 286 when housing 282 is assembled. A characterization tag 90b is disposed in characterization tag recess 310b prior to that assembly.

Again, a characterization tag recess 310c may be formed in a surface of base 284 contacted by septum support 288 when housing 282 is assembled. A characterization tag 90c can be disposed therein prior to that assembly.

Alternatively, but not illustrated, a characterization tag recess such as those described previously, can be formed in a surface of cap 286 contacted by either of septum support 288 or base 284 when those components of housing 282 are assembled.

The characterization tag utilized can be retained in the corresponding characterization tag recess therefor by a biocompatible potting material. Preferably, however, in view of the ultrasonic bonding of the components of housing 282, a silicone gel is utilized, as such tends to cushion the characterization tag from ultrasonic energy during the bonding process.

Figure 17:
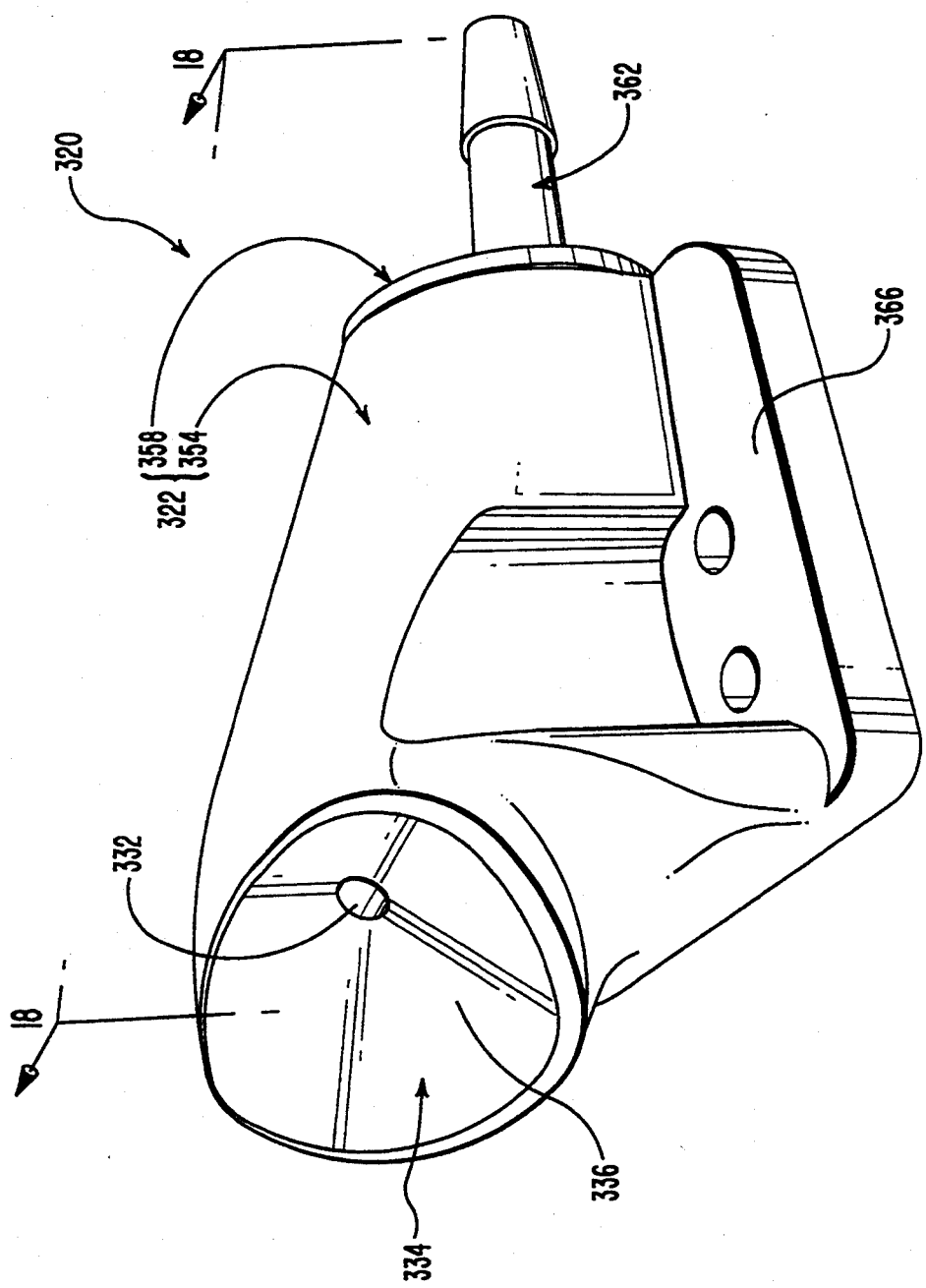
FIG. 17 is a perspective view of a fourth embodiment of an implantable access port incorporating teachings of the present invention.

FIGS. 17-19 illustrate yet another medical device 320 that can beneficially incorporate teachings of the present invention, thereby to be utilizable in the system disclosed herein. As shown there, medical device 320 comprises a style of infusion port that functions without the use of a fluid cavity or a needle-penetrable septum.

Instead, medical device 320 is accessed through skin 20 of patient 10 utilizing as an access tool a semi-rigid catheter inserted through skin 20 to medical device 320 on a solid needle. The semi-rigid catheter is entered into medical device 320, and the needle therein is withdrawn. Further advancement of the access tool opens a fluid seal in medical device 320 enabling fluid communication between the proximal end of the semi-rigid catheter outside of skin 20 of patient 10 and a catheter implanted and attached to medical device 320. The semi-rigid catheter thus comprises a tubular member introduced through the skin of the patient to communicate with the proximal end of the lumen of a catheter implanted in the body thereof.

As best understood by reference to FIG. 17 and 18 taken together, medical device 320 comprises a needle-impenetrable housing 322 enclosing and defining a number of interior spaces. These include a valve chamber 324, an outlet passageway 326 communicating between valve chamber 324 and the exterior of housing 322, and a non-linear entry passageway 328 communicating at the distal end 330 thereof with valve chamber 324 and at the proximal end 332 thereof with the exterior of housing 322. A funnel-shaped entrance orifice 334 is formed in the surface of housing 322 so as to communicate at the narrow end 336 thereof with proximal end 332 of entry passageway 328.

A semi-flexible, tubular catheter introduced on a rigid needle through skin 20 of patient 10 becomes directed by the sides of entrance orifice 334 toward proximal end 332 of entry passageway 328. Thereafter the semi-rigid catheter is able to advance the full length of entry passageway 328 into valve chamber 324, but the bend 338 in entry passageway 328 precludes the solid needle from further advancement. This protects the valving structure in valve chamber 324 from damage.

A leaflet valve 340 is captured in valve chamber 324 by housing 322, thereby to provide a selectively-openable fluid seal between entry passageway 328 and outlet passageway 326. As best appreciated by reference to FIGS. 18 and 19 together, leaflet valve 340 comprises a first leaflet valve disk 342 having formed therethrough a centrally disposed diametrically aligned first slit 344. A second leaflet valve disk 346 having a centrally disposed diametrically aligned second slit 348 formed therethrough is positioned in mating contact with first leaflet disk 342 with second slit 348 disposed at an angle to first slit 344. Finally, a sealing disk 350 having a centrally disposed aperture 352 formed therethrough is positioned in mating contact with second sealing leaflet valve disk 346 on the side thereof opposite from first leaflet valve disk 342.

Again as appreciated best by viewing FIGS. 18 and 19 together, housing 322 of medical device 320 comprises a needle-impenetrable body portion 354 which defines therewithin valve chamber 324, entry passageway 326, entrance orifice 334, and an access aperture 356 communicating through housing 322 with valve chamber 324. Access aperture 356 is located on the side of valve chamber 324 opposite from entry passageway 328.

A valve chamber plug 358 defining therewithin outlet passageway 326 is securable in access aperture 356 to capture leaflet valve 340 in valve chamber 324. Valve chamber plug 358 itself comprises a base portion 360 configured to be secured in access aperture 356 and an outlet stem 362 projecting from the side of base portion 360 opposite valve chamber 324. Outlet stem 362 encloses outlet passageway 326, and the distal end of outlet stem 362 is configured to receive the proximal end of the implanted catheter used with medical device 320.

Medical device 320 can be utilized in the inventive system disclosed herein through the attachment to housing 322 thereof of a characterization tag, such as characterization tag 90 shown in FIGS. 4 and 5 or characterization tag 180 shown in FIGS. 8 and 9. The use of the latter form of characterization tag is not illustrated herein, but several alternative placements of a characterization tag, such as characterization tag 90 can be seen in FIG. 19.

First, a characterization tag recess 264a can be formed on the suture flange 366 of housing 322. A characterization tag 90a can then be retained therein utilizing a biocompatible potting material not shown.

Alternatively, a characterization tag recess 364b can be formed elsewhere on the exterior of housing 322, thereby to receive a characterization tag 90b, which is held in place by a biocompatible potting material 368.

Finally, a characterization tag 90c can be permanently captured between body portion 354 and valve chamber plug 358 in a characterization tag recess 364c shown most clearly in FIG. 19 as being formed in a surface of valve chamber plug 358 engaged by body portion 354 when housing 322 is assembled.

Figure 20:
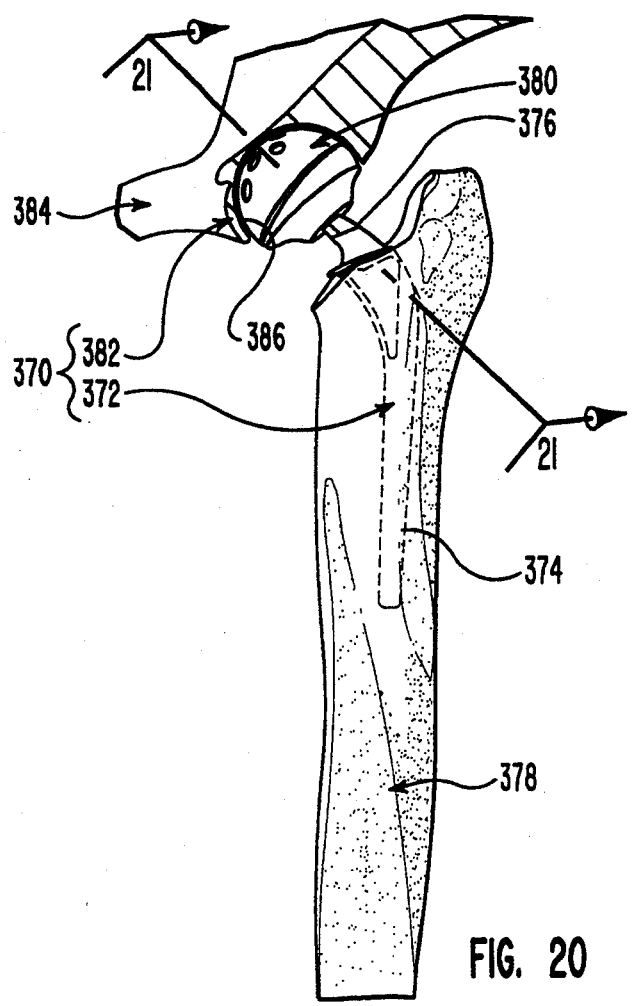
FIG. 20 is a perspective view of an implantable prosthetic hip joint incorporating teachings of the present invention shown installed between the hip bone and the femur of a patient.
Figure 21:
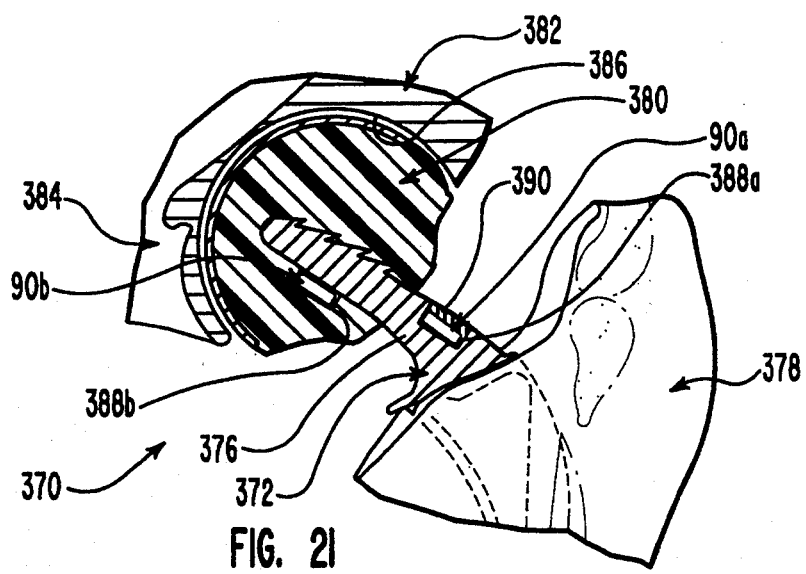
FIG. 21 is an enlarged cross-sectional plan view of the implantable prosthetic hip joint illustrated in FIG. 20 taken along section line 21—21 shown therein.

FIGS. 20 and 21 illustrate yet another medical device 370 which can beneficially incorporate teachings of the present invention. As there illustrated, medical device 370 comprises a prosthetic implant device taking the form of an artificial hip joint replacement. Medical device 370 comprises a shaft 372 having a first end 374 and a second end 376. First end 374 of shaft 372 is shown as being attached to the femur 378 of a patient. Second end 376 of shaft 372 terminates in a spherical portion 380.

Medical device 370 further comprises a cup portion 382 that is attachable to the hip bone 384 of a patient. Cup portion 382 is so configured on the side 386 thereof opposite hip bone 384 as to pivotably receive spherical portion 380 in a ball-and-socket relationship.

In order for a medical attendant of patient 10 to ascertain the nature of medical device 370 from outside body 12 of patient 10, it is necessary according to the teachings of the present invention to attach to medical device 370 a characterization tag, such as characterization tag 90 illustrated in FIGS. 4 and 5 or characterization tag 180 illustrated in FIGS. 8 and 9. The latter form of characterization tag will not be depicted herein.

Nevertheless, FIG. 21 illustrates two possible dispositions of such characterization tag as will enable medical device 370 to be utilized in the inventive system disclosed herein.

For example, a characterization tag recess 388a is formed on the exterior of shaft 372 and a characterization tag 90a is disposed and retained therein by a biocompatible potting material 390.

Alternatively, if shaft 372 is comprised of a plurality of parts, such a characterization tag can be permanently captured therebetween prior to the assembly thereof. For example, a characterization tag 90b can be disposed in a characterization recess 388b formed in a surface of spherical portion 380 engaged by the balance of shaft 372 when spherical portion 380 is assembled thereto.

The above embodiments of medical devices 14, 230, 280, 320, and 370 are offered as but examples of the types of implantable medical devices which can beneficially incorporate teachings of the present invention toward use in a system that permits the acquisition from outside the body of a patient of data pertaining to medical devices implanted therein. In each instance, the medical device with a characterization tag, such as that disclosed earlier, can be implanted in the body of a patient and be identified or otherwise characterized from the exterior thereof by scanning with a characterization probe, such as characterization probe 60. The characterization tag of the present invention carries no self-contained power source, thereby simplifying the fabrication, reducing the cost, and streamlining any regulatory approval necessary relative thereto.

The present invention comprises a combination of elements including at least an implantable medical device, a characterization tag attached thereto, and a characterization probe.

Examples of circuitry appropriate for carrying out the functions cited above for the characterization tag and the characterization probe can be found in U.S. Pat. No. 4,333,072 which issued on Jun. 1, 1982, to inventor Michael Biegel for an invention entitled "Identification Device." U.S. Pat. No. 4,333,072 is hereby explicitly and completely incorporated herein by reference. The technology disclosed in this patent is recommended therein for the purpose of identifying an animal in which the characterization tag thereof is implanted. The technology is not suggested for implantation in human subjects or for attachment to medical devices to be implanted in human subjects.

Figure 22:
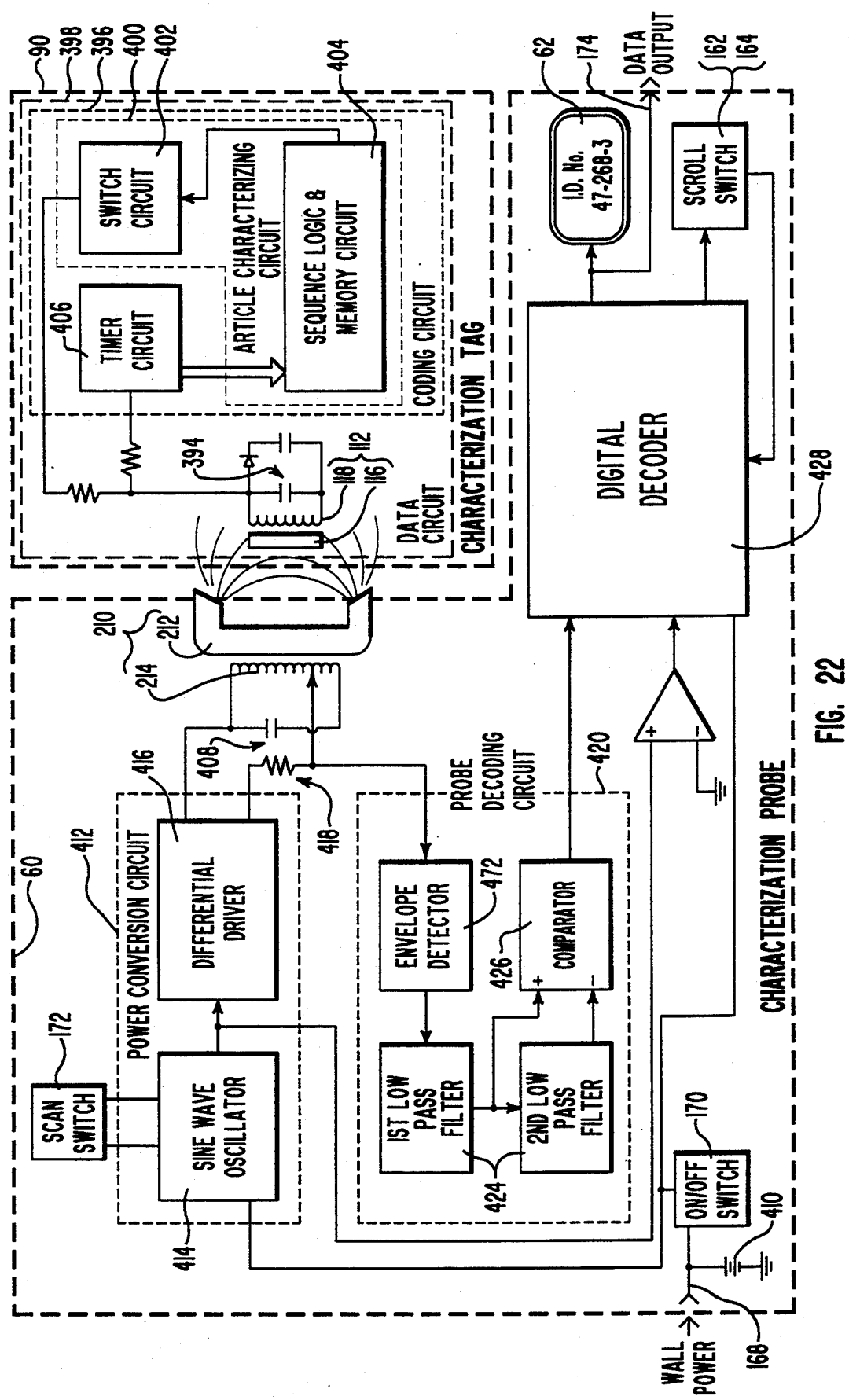
FIG. 22 is an electronic schematic diagram illustrating the major functional circuitry groupings in one embodiment of characterization tag and in one embodiment of a medical device identification probe for use in the present invention.

Illustrated in FIG. 22 is a functional electrical diagram depicting the groupings of electrical components by which specific necessary or preferable functions are performed in the characterization tag or the characterization probe of the present invention. In FIG. 22, identical reference characters are utilized to refer therein to structures depicted and disclosed earlier.

For example, in FIG. 22, the characterization tag therein is shown by way of example and not limitation as characterization tag 90 containing a field detecting coil 112 comprised of a core 116 and windings of a conductor 118. These are connected in parallel with a capacitor 394 to define a resonant circuit. A coding circuit 396 is electrically coupled to field detecting coil 112 in order to perform the functions of the coding means disclosed above. Together coding circuit 396 and the resonant circuit defined by field detecting coil 112 and capacitor 394 define a data circuit 398. Data circuit 398 is powered by energy absorbed through inductive coupling with an alternating magnetic field generated external to the body of the patient.

Coding circuit 396 comprises an article characterization means for storing data pertaining to a medical device and for reading out that data in a timed sequence by loading field detecting coil 112 in a predetermined sequence of loading conditions. As shown by way of example and not limitation in FIG. 22, an article characterizing circuit 400 is provided toward that end. Coding circuit 396 also comprises timer means electrically coupled between field detecting coil 112 and article characterizing circuit 400 for driving article characterizing circuit 400 to read out the data therein in response to a data circuit signal produced by magnetic coupling of an alternating magnetic field with field detecting coil 112.

As shown by way of example and not limitation, article characterizing circuit 400 comprises an electrical load, a switching circuit 402 for selectively coupling and uncoupling that load to field detecting coil 112, and memory means coupled to switching circuit 402 for storing data pertaining to a medical device and for reading out that data by driving switch circuit 402 in a timed sequence corresponding to that data. The memory means of the present invention may take the form of a sequence logic memory circuit 404 which stores data pertaining to a medical device and drives switch circuit 402. The timer means of the present invention comprises a timer circuit 406 coupled between field detecting coil 112 and sequence logic and memory circuit 404. Timer circuit 406 is activated by a data signal circuit to drive sequence logic and memory circuit 404.

Also shown in FIG. 22 are the electrical components of characterization probe 60. These include a field generating coil, such as field generating coil 210 comprised of a C-shaped core 212 and windings of a conductor 214 thereon. A capacitor 408 connected parallel to field generating coil 210 defines therewith a resonant circuit.

Power by which to generate a magnetic field from field generating coil 210 is delivered thereto by way of power switch 170, either from standard wall power or from a battery 410. In the latter instance, a power conversion circuit 412 is provided which, being coupled to battery 410, converts direct current therefrom into alternating electric power to be delivered to field generating coil 210. Power conversion circuit 412 is shown by way of example as comprising a sine wave oscillator 414 and a differential driver 416.

Scan switch 172 permits characterization probe 60 to be operated on a low level of power when a magnetic field is not required to be generated by field generating coil 210.

The voltage appearing, for example, across a resistor 418 connected in series with field generating coil 210 produces a probe signal that reflects variations in the amount of energy absorbed from the alternating magnetic field produced by field generating coil 210 by the predetermined sequence of loading condition imposed on field detecting coil 112 by article characterizing circuit 400. The probe signal is then processed in a probe decoding circuit 420 to produce a digital data signal corresponding to variations in the amount of energy absorbed from the alternating magnetic field generated by field generating coil 210.

As shown by way of example in FIG. 22, probe decoding circuit 420 comprises an envelope detector 422, low pass filters 424, and a comparator 426 coupled as illustrated. The digital data signal produced thereby is correlated in a digital decoder 428 to data stored therein relative to potential implanted medical devices. As a result thereof, data pertaining to the medical device in which characterization tag 90 is implanted will appear on display screen 62. If that data is excessive to the capacity of screen 62, the data can be viewed through the action of scrolling switch 162, 164.

The above electrical circuitry is but exemplary of the type of electrical circuitry utilizable in a combination comprising the present invention. Specific details of circuitry forming such functions can be located in the aforementioned U.S. Pat. No. 4,333,072.

The present invention also contemplates a method for the acquisition from outside the body of a patient of data pertaining to a medical device implanted therein. In brief overview, that method comprises the steps of securing to a medical device a characterization tag such as described above, surgically implanting the medical device with the characterization tag secured thereto at a predetermined implant location in the body of a patient, generating an alternating magnetic field external to the body of the patient in the vicinity of the implant location, and then sensing variations in the amount of energy absorbed from that alternating magnetic field by the characterization tag.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for permitting the acquisition from outside the body of a patient of data pertaining to medical devices implanted therein, the system comprising:
   (a) a medical device capable of subcutaneous implantation at a predetermined implant location in the body of the patient;
   (b) a medical device data circuit secured to said medical device prior to the implantation thereof, said data circuit being powered by energy absorbed through the mutual inductive coupling thereof with an alternating magnetic field generated external to the body of the patient, said data circuit comprising:
      (i) field detection means for inductively coupling with said alternating magnetic field, and responsive thereto for generating a data circuit signal; and
      (ii) coding means electrically coupled to said field detection means for selectively loading and unloading said field detection means in a predetermined sequence of loading conditions responsive to said data circuit signal, said sequence of loading conditions corresponding to data pertaining to said medical device, and said loading and unloading of said field detection means correspondingly varying the amount of said energy absorbed from said alternating magnetic field in generating said data circuit signal; and
   (c) a medical device characterization probe movable external to the body of the patient in the vicinity of said implant location, said identification probe comprising:
      (i) field generation means coupleable to a source of alternating electric power for generating said alternating magnetic field; and
      (ii) sensor means electrically coupled to said field generation means for producing a probe signal reflecting variations in said amount of said energy absorbed from said alternating magnetic field by said data circuit.

2. A system as recited in claim 1, wherein said characterization probe further comprises digital decoding means electrically coupled to said sensor means for processing said probe signal to produce a digital data signal corresponding to said variations in said amount of said energy absorbed from said alternating magnetic field by said data circuit and for correlating said digital data signal with said data pertaining to said medical device.

3. A system as recited in claim 2, wherein said characterization probe further comprises display means electrically coupled to said digital decoding means for giving a visual indication of said data pertaining to said medical device.

4. A system as recited in claim 1, wherein said coding means comprises:
   (a) article characterization means for storing data pertaining to said medical device and for reading out said data in a timed sequence by loading said field detection means in said predetermined sequence of loading conditions; and (b) timer means electrically coupled between said field detection means and said article characterization means for driving said article characterization means to read out said data in response to said data circuit signal.

5. A system as recited in claim 4, wherein said article characterization means comprises:

(a) an electrical load;

(b) a switching circuit for selectively coupling and uncoupling said load to said field detection means; and (c) a memory means coupled to said switching circuit for storing said data pertaining to said medical device and for reading out said data by driving said switching circuit in a timed sequence corresponding to said data.

6. A system as recited in claim 5, wherein said timing means comprises a timer circuit coupled between said field detection means and said memory means, said timer circuit being activated by said data circuit signal to drive said memory means to read out said data.

7. A system as recited in claim 1, wherein said medical device comprises an implantable access port.

8. A system as recited in claim 7, wherein said implantable access port comprises a needle-impenetrable housing enclosing a first fluid cavity and defining a first access aperture through said housing communicating with said first fluid cavity.

9. A system as recited in claim 8, wherein a data circuit recess is formed on the exterior of said housing, and said data circuit is disposed in said data circuit recess.

10. A system as recited in claim 9, wherein said data circuit is retained in said data circuit recess by a biocompatible potting material.

11. A system as recited in claim 8, wherein said housing comprises:

(a) a generally planar floor;

(b) a top wall disposed opposite said floor generally parallel thereto, said first access aperture being formed through said top wall of said housing;

(c) side walls extending from the periphery of said floor to the periphery of said top wall; and (d) a needle-penetrable material encasing the exterior of said floor of said housing and the exterior of portions of said side walls adjacent thereto.

12. A system as recited in claim 11, wherein said data circuit is disposed against said exterior of said floor between said housing and said needle-penetrable material.

13. A system as recited in claim 11, wherein said data circuit is disposed against the exterior of one of said side walls between said housing and said needle-penetrable material.

14. A system as recited in claim 8, wherein said housing comprises a plurality of components, and wherein said data circuit is permanently captured between a pair of said components.

15. A system as recited in claim 8, wherein said housing comprises:

(a) a base having a flat floor and walls normal to an upstanding therefrom, said walls defining said first fluid cavity; and (b) a cap configured to receive said base, said cap comprising:

(i) a top wall having formed therein said first access aperture at a position opposite said first fluid cavity when said base is received in said cap; and (ii) a skirt depending from the periphery of said top wall, said skirt enclosing said walls of said base when said cap is received in said base.

16. A system as recited in claim 15, wherein a data circuit recess is formed in a surface of said base contacted by said cap when said base is received in said cap, and wherein said data circuit is disposed in said data circuit recess prior to said base being received in said cap.

17. A system as recited in claim 15, wherein a data circuit recess is formed in a surface of said cap contacted by said base when said base is received in said cap, and wherein said data circuit is disposed in said data circuit recess prior to said base being received in said cap.

18. A system as recited in claim 8, wherein said implantable access port further comprises a needle-penetrable septum captured by said housing and sealing said first access aperture.

19. A system as recited in claim 8, wherein said implantable access port comprises:

(a) a needle-impenetrable housing enclosing and defining the following:

(i) a valve chamber;

(ii) an outlet passageway communicating between said valve chamber and the exterior of said housing;

(iii) a non-linear entry passageway communicating at the distal end thereof with said valve chamber and at the proximal end thereof with the exterior of said housing; and (iv) a funnel-shaped entrance orifice formed in the surface of said housing communicating at the narrow end thereof with said proximal end of said entry passageway; and (b) a leaflet valve captured in said valve chamber by said housing, thereby to provide a selectively-openable fluid seal between said entry passageway and said outlet passageway.

20. A system as recited in claim 8, wherein said housing further encloses a second fluid cavity and defines a second access aperture communicating through said housing with said second fluid cavity.

21. A system as recited in claim 20, wherein a data circuit recess is formed on the exterior of said housing, and said data circuit is disposed in said data circuit recess.

22. A system as recited in claim 21, wherein said data circuit is retained in said data circuit recess by a biocompatible potting material.

23. A system as recited in claim 20, wherein said housing comprises:

(a) a generally planar floor;

(b) a top wall disposed opposite said floor generally parallel thereto, said first access aperture and said second access aperture being formed through said top wall of said housing;

(c) side walls extending from the periphery of said floor to the periphery of said top wall;

(d) an inner wall extending between said floor, said top wall, and opposed portions of said side walls, thereby to define on opposite sides of said inner wall said first fluid cavity and said second fluid cavity, respectively.

24. A system as recited in claim 20, wherein said housing comprises a plurality of components, and wherein said data circuit is permanently captured between a pair of said components.

25. A system as recited in claim 20, wherein said housing comprises:
(a) a base having a flat floor and walls normal to and upstanding therefrom, said walls defining said first fluid cavity and said second fluid cavity;
(b) a planar septum support configured to mate with the ends of said walls of said base opposite said floor of said base, said septum support having formed therethrough a first septum receiving aperture positioned above said lo first fluid cavity and a second septum receiving aperture position above said second fluid cavity; and
(c) a cap configured to receive said septum support and said base, said cap comprising;
(i) a top wall having formed therein a first septum access aperture at a position opposite said first septum receiving aperture when said septum support and said base are received in said cap and a second access aperture at a position opposite said second septum receiving aperture when said septum support and said base are received in said cap; and
(ii) a skirt depending from the periphery of said top wall of said cap, said skirt enclosing said septum support and said walls of said base when said septum support and said base are received in said cap.

26. A system as recited in claim 25, wherein a data circuit recess is formed in a surface of said base contacted by said septum support when said septum support mates with said ends of said walls of said base opposite from said floor of said base, and wherein said data circuit is disposed in said data circuit recess prior to the mating of said septum support with said ends of said walls of said base.

27. A system as recited in claim 25, wherein a data circuit recess is formed in a surface of said septum support contacted by said cap when said base and said septum support are received in said cap, and wherein said data circuit is disposed in said data circuit recess prior to said base and said septum support being received in said cap.

28. A system as recited in claim 25, wherein a data circuit recess is formed in a surface of said base contacted by said cap when said base and said septum support are received in said cap, and wherein said data circuit is disposed in said data circuit recess prior to said base and said septum support being received in said cap.

29. A system as recited in claim 20, wherein said implantable access port further comprises:
(a) a first needle-penetrable septum captured by said housing and sealing said first access aperture; and
(b) a second needle-penetrable septum captured by said housing and sealing said second access aperture.

30. A system as recited in claim 1, wherein said field detection means comprises an induction coil secured to said medical device and electrically coupled to said coding means.

31. A system as recited in claim 1, wherein said field generation means comprises an induction coil housed in said characterization probe and electrically coupled to said sensor means.

32. A system as recited in claim 1, wherein said field generation means comprises a first resonant circuit housed in said identification probe and comprising components defining a first resonant frequency associated therewith, said first resonant circuit comprising:
(a) a first induction coil housed in said characterization probe and being electrically coupled to said sensor means; and
(b) a first capacitor connected in parallel to said first induction coil.

33. A system as recited in claim 32, wherein said first induction coil comprises:
(a) a core; and
(b) a conductor wrapped said core.

34. A system as recited in claim 33, wherein said core is comprised of a ferrous material.

35. A system as recited in claim 33, wherein said core assumes a generally elongate shape having a longitudinal axis, and said longitudinal axis is oriented toward the skin of the patient when said characterization probe is moved external to the body of the patient in the vicinity of said implant location.

36. A system as recited in claim 33, wherein said core is generally C-shaped.

37. A system as recited in claim 33, wherein said core terminates in first and second non-parallel, flat, flux-transmitting surfaces, said first and second flux-transmitting surfaces defining corresponding first and second flux-transmitting planes, said first and second flux-transmitting planes forming a dihedral angle the interior of which is oriented toward the skin of the patient when said characterization probe is moved external to the body of the patient in the vicinity of said implant location.

38. A system as recited in claim 32, wherein said field detection means comprises a second resonant circuit secured to said medical device and comprising components defining a second resonant frequency associated therewith, said second resonant circuit comprising:
(a) a second induction coil secured to said medical device and being electrically coupled to said coding means; and
(b) a second capacitor connected in parallel to said second induction coil.

39. A system as recited in claim 38, wherein said second resonant frequency is substantially equal to said first resonant frequency.

40. A system as recited in claim 1, wherein said medical device comprises an implantable prosthetic article.

41. A system as recited in claim 40, wherein said prosthetic article comprises a hip joint transplant.

42. A system as recited in claim 41, wherein said hip joint transplant comprises:
(a) a shaft having first and second ends, said first end of said shaft being attachable to the femur of the patient, and said second end of said shaft terminating in a spherical portion; and
(b) a cup portion attachable to the hip bone of the patient, said cup portion being so configured on the side thereof opposite the hip bone of the patient as to pivotably receive said spherical portion of said shaft in a ball-and-socket relationship.

43. A system as recited in claim 42, wherein a data circuit recess is formed on the exterior of said shaft of said hip joint transplant, and said data circuit is disposed in said data circuit recess.

44. A system as recited in claim 43, wherein said data circuit is retained in said data circuit recess by a biocompatible potting material.

* * * * *

UNITED STATES PATENT AND TRADEMARK OFFICE
CERTIFICATE OF CORRECTION

PATENT NO. : 5,423,334
DATED : June 13, 1995
INVENTOR(S) : GUY J. JORDAN

It is certified that error appears in the above-indentified patent and that said Letters Patent is hereby corrected as shown below:

Column 13, line 1, "case of medical device," should be --case of a medical device,--
Column 13, lines 11-12, "but many instances" should be --but in many instances--
Column 13, line 17, "medial attendant" should be --medical attendant--
Column 15, line 28, "and thus comprised" should be --and thus be comprised--
Column 15, line 34, "a integrated" should be --an integrated--
Column 16, line 34, "There-coating" should be --There, coating--
Column 16, line 48, "contact 134, 138" should be --contacts 134, 138--
Column 16, line 49, "opposes and contact" should be --opposes and contacts--
Column 18, line 11, "screen 26" should be --screen 62--
Column 18, line 62, "housing 60" should be --housing 160--
Column 20, line 23, "a generally elongate shape" should be --a generally elongated shape--
Column 21, line 36, "there through" should be --therethrough--
Column 22, lines 28-29, delete "is produced"
Column 23, line 7, "septums 290" should be --septum 290--
Column 23, line 12, "an upstanding therefrom" should be --and upstanding therefrom--
Column 23, line 29, "not illustrated FIGS. 15 and 16" should be --not illustrated in FIGs. 15 and 16,--

UNITED STATES PATENT AND TRADEMARK OFFICE
CERTIFICATE OF CORRECTION

PATENT NO.   : 5,423,334
DATED        : June 13, 1995
INVENTOR(S)  : GUY J. JORDAN It is certified that error appears in the above-indentified patent and that said Letters Patent is hereby corrected as shown below:

```
Column  1, line 45, "medical devices" should be --medical device--
Column  3, line 24, "of the nature" should be --or the nature--
Column  3, line 51, "condition" should be --conditions--
Column  3, line 63, delete "an"
Column  4, line 14, "patent" should be --patient--
Column  4, line 38, "forgoing" should be --foregoing--
Column  5, line 7, "can not" should be --cannot--
Column  5, line 27, delete "are"
Column  6, lines 11-12, "elementing" should be --eliminating--
Column  6, line 26, "patent" should be --patient--
Column  7, line 2, "the present" should be --the present invention--
Column  7, line 34, "and encapsulated" should be --are encapsulated--
Column  7, line 36, "an disc-type configuration" should be --a disc-type configuration--
Column  7, line 37, "maybe" should be --may be--
Column  9, line 7, "is described" should be --as described--
Column 10, line 24, "FIGS. 7" should be --FIG. 7--
Column 10, line 49, "is an cross-sectional elevation view" should be --is a cross-sectional elevation view--
Column 11, line 60, "corresponding an" should be --corresponding to an--
Column 12, line 22, "there through" should be --therethrough--
Column 12, line 24, "in region" should be --in a region--
Column 12, line 30, "absence" should be --absent--
Column 12, line 40, delete "were"
Column 12, line 42, "where" should be --were--
```

UNITED STATES PATENT AND TRADEMARK OFFICE
CERTIFICATE OF CORRECTION

PATENT NO. : 5,423,334
DATED : June 13, 1995
INVENTOR(S) : GUY J. JORDAN

It is certified that error appears in the above-indentified patent and that said Letters Patent is hereby corrected as shown below:

Column 31, line 14, delete "lo"
    Column 31, line 15, "position" should be --positioned--
    Column 32, line 1, "identification probe" should be --characterization probe--
    Column 32, line 12, "wrapped said core" should be --wrapped around said core--

Signed and Sealed this

Twenty-ninth Day of October 1996

Attest:

BRUCE LEHMAN

*Attesting Officer*      *Commissioner of Patents and Trademarks*